United States Patent [19]
Hoye et al.

[11] Patent Number: 5,849,936
[45] Date of Patent: Dec. 15, 1998

[54] METHOD FOR THE SYNTHESIS OF BIS-TETRAHYDROFURANYL ANNONACEOUS ACETOGENINS

[75] Inventors: Thomas R. Hoye, St. Paul; Lushi Tan, Minneapolis, both of Minn.

[73] Assignee: Regents of the Univeristy of Minnesota, Minneapolis, Minn.

[21] Appl. No.: 686,261

[22] Filed: Jul. 25, 1996

Related U.S. Application Data

[62] Division of Ser. No. 405,131, Mar. 15, 1995, Pat. No. 5,587,491.

[51] Int. Cl.$^6$ .................................................. C07D 307/58
[52] U.S. Cl. .............................................................. 549/313
[58] Field of Search ............................................. 549/313

[56] References Cited

PUBLICATIONS

K. I. Ahammadsahib, et al., "Mode of Action of Bulltactin: A Potent Antitumor and Pesticidal Annonaceous Acetogenin", *Life Sciences*, 53, 1113–1120 (1993).

M. Degli Esposti, et al., "Natural Substances (Acentogenins) from the Family Annonaceous are Powerful Inhibitors of Mitochondrial NADH Dehydrogenases (Complex I)", *Biochem. J.*, 301 161–167 (1994).

W. P. Fang, et al., "Gigantetrocin and Gigantriocin: Two Novel Bioactive Annonaceous Acetogenins from *Goniothalamus giganteus*", *Heterocycles*, 32, 11–17 (1991).

X. P. Fang, et al., "Annonaceous Acetogenins: an Updated Review", *Phytochem. Anal.*, 4, 27–48 (1993).

X. P. fang, et al., "Annonaceous Acetogenins: an Updated Review–Appendices", *Phytochem. Anal.*, 4, 49–67 (1993).

B. Figadere, et al., "Synthesis of 2,33–Dihydro–4–Oxo–Murisolin: Conjugate Addition of Primary Alkyl Iodides to alpha, beta–Unsaturated Ketones", *Tet. Lett.*, 33, 5189–5192 (1992).

T. R. Hoye, et al., "On the Stereochemistry of the Bistetrahydrofuranyl Moiety of Uvaricin: Protron Chemical Shifts Can Play a Crucial Role in Complex Structure Determination", *J. Am. Chem. Soc.*, 109, 4402–4403 (1987).

T. R. Hoye, et al., "Synthesis of (+)–(15,16,19,20,23,24)–hexepi–Uvacin: a Bis(tetrahydrofuranyl) Annonaceous Acetogenin Analog", *J. Am. Chem. Soc.*, 113, 9369–9371 (1991).

T. R. Hoye, et al., "Synthesis of (–)–Bullatactin: The Enantiomer of a Potent, Antitumore, 4–Hydroxylated, Annonaceous Acetogeninc", *Tet. Lett.*, 34, 5043–5046 (1993).

Y. H. Hui, et al., "Bullatacin and Bullatacinone: Two Highly Potent Bioactive Acetogenins from Annona bullata", *J. Nat. Prod.*, 52, 463–477 (1989).

U. Koert, "Total Synthesis of (+)–Rolliniastatin 1", *Tet. Lett.*, 35, 2517–2520 (1994).

M. A. Lewis, et al., "Inhibition of Respiration of Site I by Asimicin, an Insecticidal Acetogenin of the Pawpaw, Asimina triloba (Annonaceae)", *Pesticide Biochem. Physiol.*, 45, 15–23 (1993).

M. Londershausen, et al., "Molecular Mode of Action of Annonins", *Pestic. Sci.*, 33, 427–438 (1991).

H. Makabe, et al., "Total Synthesis of Solamin and Reticulatacin", *J. Chem. Soc. Perkin Trans.*, 1, 1975–1981 (1994).

M. J. Rieser, et al., "Determination of Absolute Configuration of Stereogenic Carbinol Centers in Annonaceous Acetogenins by 1H–and 19F–NMR Analysis of Mosher Ester Derivatives", *J. Am. Chem. Soc.*, 114, 10203–10213 (1992).

J. K. Rupprecht, et al., "Annonaceous Acetogenins: A Review", *J. Nat. Prod.*, 53, 237–278 (1990).

B. M. Trost, "A Concise Convergent Strategy to Acetogenins, (+)–Solamin and Analogues", *J. Am. Chem. Soc.*, 116, 7459–7460 (1994).

Z. J. Yao, et al, "Total Synthesis of (10x,15R,16S,19S,20S, 34R)–Corossoline", *Tet. Lett.*, 35, 157–160 (1994).

*Primary Examiner*—Ba K. Trinh
*Attorney, Agent, or Firm*—Schwegman, Lundberg, Woessner, & Kluth, P.A.

[57] ABSTRACT

A method for the synthesis of bis-tetrahydrofranyl Annonaceous acetogenins, including the natural products and analogs thereof, is provided which proceeds by the Pd-mediated coupling of a bis-tetrahydrofuranyl-subunit comprising a terminal alkyne, with a (C4)-hydroxybutenolide subunit comprising a terminal vinyl iodide, followed by selective reduction of the resulting enyne.

4 Claims, 3 Drawing Sheets

METHOD FOR THE SYNTHESIS OF BIS-TETRAHYDROFURANYL ANNONACEOUS ACETOGENINS

This is a division of application Ser. No. 08/405,131, filed Mar. 15, 1995 now U.S. Pat. No. 5,587,491.

This invention was made with the support of grants GM-34492 and GM-35962 awarded by the DHHS. The U.S. Government has certain rights in the invention.

BACKGROUND OF THE INVENTION (+)-Asimicin (1) and (+)-bullatacin (2)—bis-tetrahydrofuranyl, 4-hydroxylated, Annonaceous acetogenins—represent two of the structurally most complex and biologically potent members of this abundant family of antitumor and pesticidal natural products. (+)-Bullatacin possesses remarkable levels both of cytoxicity against many human tumor cell lines, a feature shared by a number of the 4-hydroxylated acetogenins, and in vivo antitumor activity. For example, see J. K. Rupprecht et al., *J. Nat. Prod.*, 53, 237 (1990); X. Fang et al., *Phytochem. Anal.*, 4, 27 and 49 (1993); and K. Ahammadsahib et al., *Life Sci.*, 53, 1113 (1993). (+)-Bullatacin and (+)-asimicin interfere with mitochondrial electron transport processes by interaction with complex I. See, M. Landers-Hausen et al., *Pestic. Sci.*, 33, 427 (1991), M. Espositi et al., *Biochem. J.* 3,01, 161 (1994) and M. A. Lewis et al., *Pesticide Biochem. Physiol.*, 45, 15 (1993).

The relative configurations within the bis-THF portions of asimicin and bullatacin were deduced by application of the $^1$H NMR chemical shift correlation method developed for uvaricin. (T. Hoye et al., *J. Amer. Chem. Soc.*, 109 4402 (1987); J. K. Rupprecht et al., *Heterocycles*, 52, 463 (1989); Y. -H. Hui et al., *J. Nat. Prod.*, 52, 463 (1989). Details of the entire relative and absolute stereostructure of (+)-asimnicin (1) and (+)-bullatacin (2) were unraveled only recently following extensive analysis of Mosher esters of the natural products, by M. J. Rieser et al., *J. Amer. Chem. Soc.*, 114, 10203 (1992); and T. R. Hoye et al., *Tet. Lett.*, 34, 5043 (1993). The structures of these compound are depicted below:

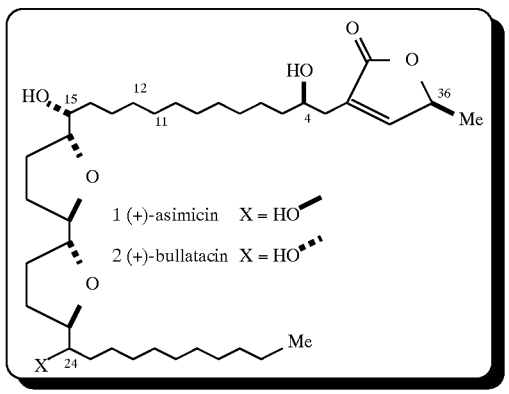

Three syntheses of bis-tetrahydrofuranyl (THF) Annonaceous acetogenins or their stereoisomers have been described. (T. R. Hoye et al., *J. Amer. Chem. Soc.*, 113, 9369 (1991); T. R. Hoye et al., *Tet. Lett.*, 34, 5043 (1993); and U. Koert et al., *Tett. Lett.*, 35, 2517 (1994)). However, the majority of efforts to date have focused on the simpler mono-THF acetogenin targets. For example, see B. Figadere et al., *Tett. Lett.*, 33, 5189 (1992); Z. -J. Yao et al., *Tett. Lett*35, 157 (1994); H. Makabe et al., *J. Chem. Soc. Perkin Trans. I*, 1975 (1994); and B. M. Trost et al., *J. Amer. Chem. Soc.*, 116, 7459 (1994).

Therefore, a need exists for efficient methods to synthesize the Annonaceous acetogenins and their analogs, particularly those which comprise the (C4)-hydroxyl group.

SUMMARY OF THE INVENTION

The present invention provides a method for preparing an acetogenin of formula (I):

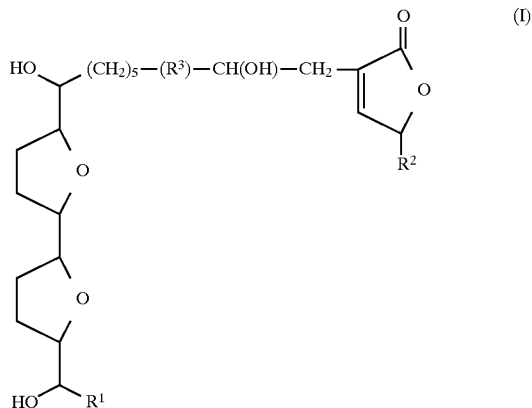

wherein $R^1$, $R^2$ and $R^3$ alkyl or aryl; comprising the steps of
(a) coupling a vinyl iodide of formula II:

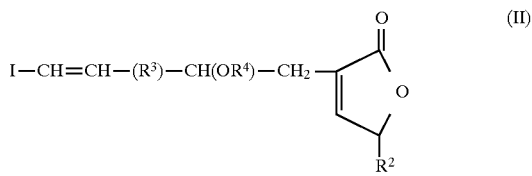

wherein $R^4$ is a removable hydroxy protecting group, with a compound of formula (III):

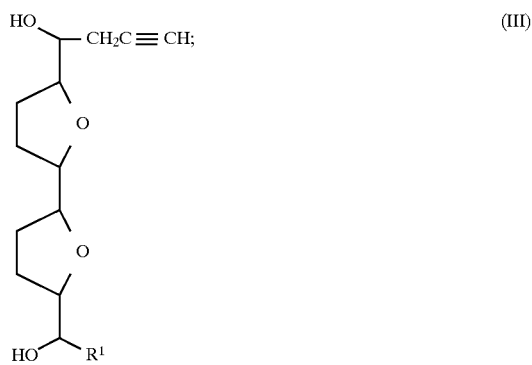

in the presence of an effective amount of a palladium catalyst, CuI and a base, in an organic solvent, to yield a enyne of the formula IV:

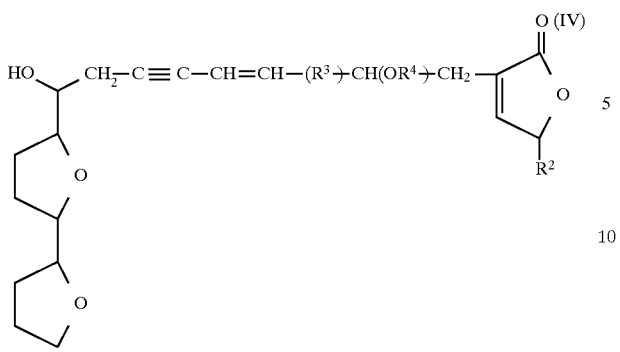

(b) hydrogenating the enyne of formula IV and removing the hydroxy protecting group to yield a compound of formula I.

A further embodiment of the invention provides a method for the preparation of a compound of formula (II):

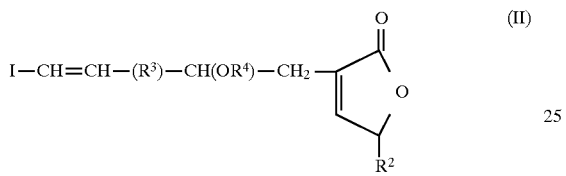

wherein $R^3$ is alkyl or aryl, $R^4$ is H or a removable hydroxyl protecting group and $R^2$ is alkyl or aryl, comprising:

(a) reacting to an epoxide of formula (V):

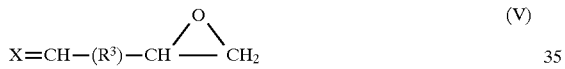

wherein X is a removable aldehyde protecting group with a compound of formula (VI):

LiC≡C—CH(OP)$R^2$    (VI)

wherein P is a removable hydroxy protecting group that is more labile than $R^4$, to yield a compound of formula (VII):

X=CH—($R^3$)—CH(O$R^4$)—CH$_2$—C≡C—CH(OP)$R^2$   (VII)

wherein $R^4$ is H;

(b) reacting O$R^4$ with a removable hydroxyl protecting group that is less labile than P and removing P to yield a compound of formula (VII) wherein P is H and $R^4$ is a hydroxyl protecting group;

(c) reacting the C≡C moiety with sodium bis(2-(methoxy)ethoxy) aluminum hydride, followed by addition of iodine to the reaction product to yield a compound of formula (VIII):

X=CH—($R^3$)—CH(O$R^4$)—CH$_2$—C(I)=CH—CH(OH)$R^2$  (VIII);

(d) reacting the moiety C(I)=CH—CH(OH)$R^2$ with carbon monoxide in the presence of a Pd(O) catalyst to yield a compound of formula (IX):

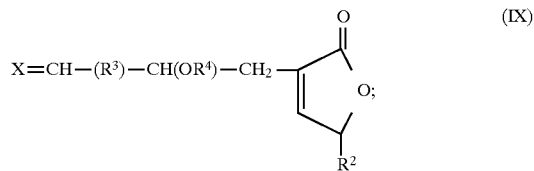

(e) removing the aldehyde protecting group to yield a compound of formula IX when X is O; and (f) converting the aldehyde moiety O=CH— to the moiety I—CH=CH— to yield a compound of formula II wherein $R^4$ is a hydroxyl-protecting group and, optionally, removing the hydroxyl protecting group to yield a compound of formula II, wherein $R^4$ is H.

Yet another embodiment of the invention provides a method for the synthesis of a compound of formula (III):

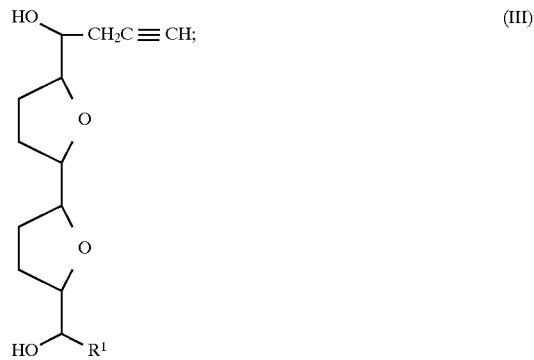

comprising the steps of:

(a) reacting a compound of formula (X):

with a hydroxy protecting group to yield a compound of formula X wherein H has been replaced by $R^7$, wherein $R^7$ is a removable hydroxy protecting group;

(b) reducing the lactone of compound (X) to yield a 3-hydroxyaldehyde of formula XI:

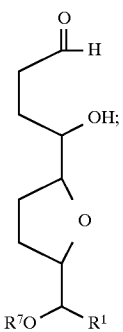

(XI)

(c) reacting the moiety C(O)H with $Ph_3P=CO_2R^8$ wherein $R^8$ is $(C_1-C_4)$alkyl, and reducing the resultant ester to yield a compound of formula (XII):

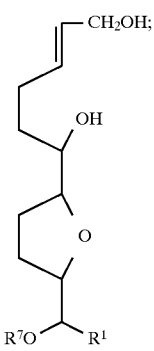

(XII)

(d) reacting the compound of formula XII with a peroxide in the presence of a Ti(IV) catalyst and base to yield a compound of the formula (XII):

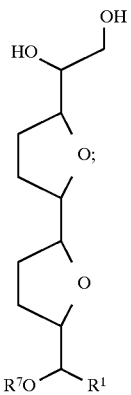

(XIII)

(e) protecting the primary hydroxyl group, and converting the secondary hydroxy group of XIII to a displacable group (OL) to yield a compound of the formula (XIV):

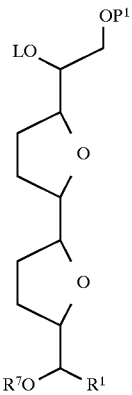

(XIV)

wherein $P^1$ is a removable hydroxy protecting group and L preferably is tosyl, mesyl or trifyl;

(f) reacting compound XIV with tetrabutylammonium fluoride in an organic solvent to yield a compound of formula (XV):

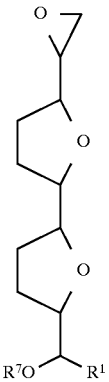

(XV)

wherein $R^7$ is H, and;

(g) reacting the epoxide moiety with $Li-C{\equiv}C-P^2$ wherein $P^2$ is a removable protecting group, followed by removal of $P^2$ to yield the compound of formula III. Preferably $R^2$ is lower alkyl, i.e., $(C_1-C_4)$alkyl, $R^3$ is $(C_3-C_{15})$alkylene and $R^1$ is $(C_5-C_{15})$alkyl.

Novel compounds of formulas I–XV are also within the scope of the invention, as are intermediates for the preparation thereof, as disclosed herein below.

DETAILED DESCRIPTION OF THE INVENTION

Figure 1:
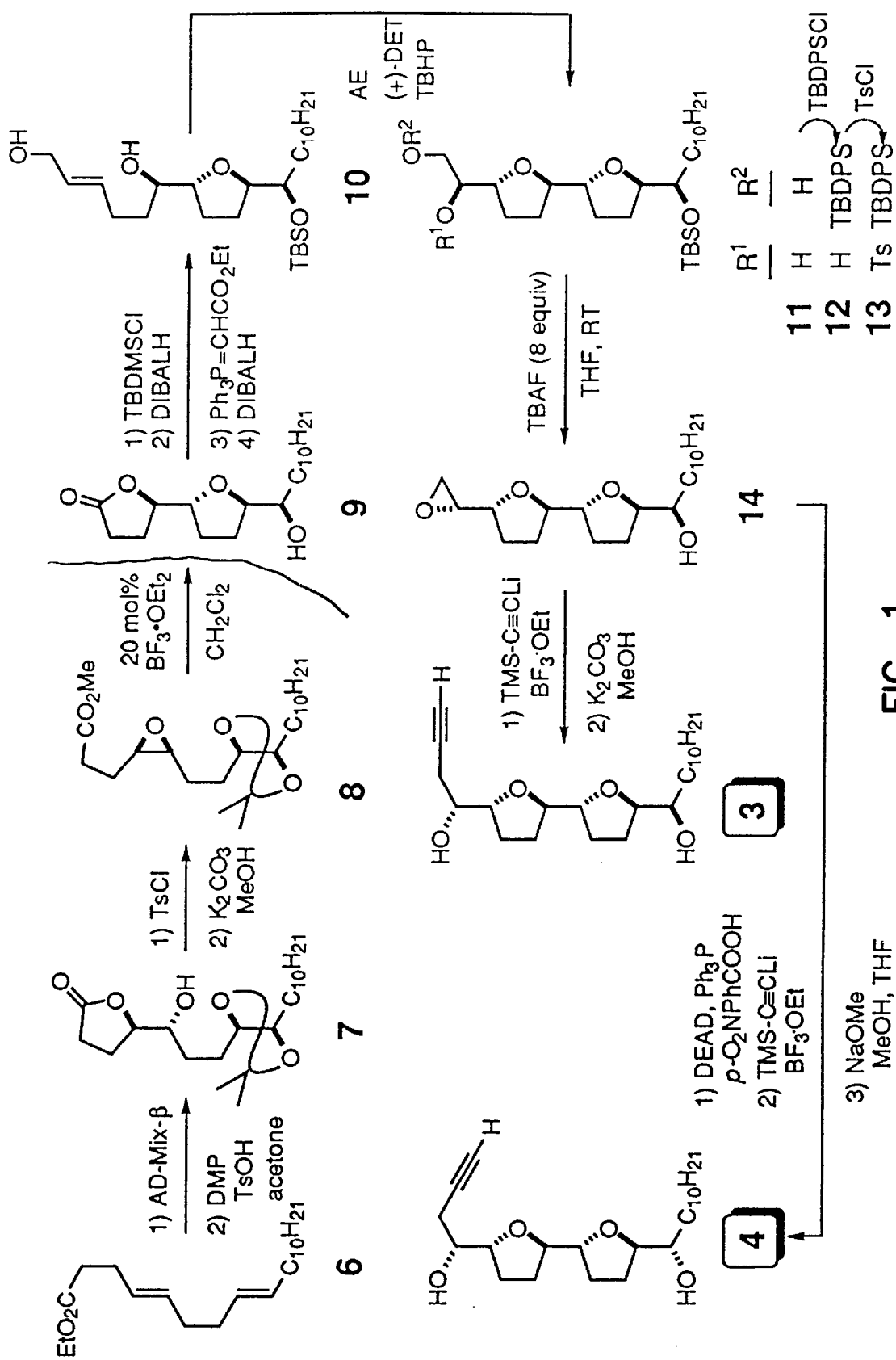

The compounds of formulas I–XV are depicted in accord with standard organic structural formulas, e.g., positions shown as unoccupied are occupied by H. The stereochemistry at the asymmetric carbon atoms is not designated. However, the individual dl-and resolved enantiomers are within the scope of the invention, and may be prepared as described in detail hereinbelow, or in the publications incorporated by reference herein. For example, the two linked tetrahydrofuranyl rings can be either of the two cis configurations, as shown in structure 1, or as in (−)-bullatacin, or can be in either of the two possible trans-configurations, for any of the compounds shown above.

The term "alkyl" as used herein encompasses branched- and straight-chain alky, i.e., $(C_1-C_{22})$alkyl, as well as cycloalkyl, (cycloalkyl)alkyl and alkyl(cycloalkyl)alkyl of about 5–25 carbon atoms. The term "aryl" as used herein encompasses $(C_6-C_{20})$aryl, including alkaryl, arakyl or alkarylakyl.

Preferably, $R^2$ is $(C_1-C_4)$alkyl, e.g., $CH_3$ or $CH_2CH_3$; $R^3$ is $(CH_2)_n$, wherein n is 2–10; preferably 3–7; e.g., pentenyl; and $R^1$ is 3–20, preferably 5–15, i.e., n-decyl.

Removable hydroxy protecting groups are selected from the wide variety of such groups known to the art are stable (or labile) to the subsequent reaction conditions, as desired. Such groups include tetrahydropyran-2-yl, 2-methoxyethoxy, acetyl, benzyl, t-Boc and $Si(R^{10})_3$ wherein each $R^{10}$ is individually $(C_1-C_4)$alkyl or phenyl. Useful aldehyde protecting include ketals, dithianes, and thioketals, e.g. [((Alkyl)O)$_2$CH]. These groups can be removed under acidic conditions, i.e., by exposure to dilute aqueous acid, and optionally with Hg(II) in the case of sulfur-containing groups. For a further discussion of labile hydroxy and carbonyl protecting groups, see U.S. Pat. No. 4,816,586, at Cols. 4–5.

Usefuil organic solvents are there which are stable to the reagents employed in the present methods, and include tetrahydrofuran, methylene chloride, DMF, DMA, ethers, benzene, toluene, hydrocarbon solvents and, in some cases, alkanols or alkanol/water mixtures.

Bases can be selected from inorganic bases such as carbonates, bicarbonates, borates and hydroxides, or organic bases such as amines, acetates, morpholine, pyridines, tartarates, citrates and the like. Acids include inorganic or organic acids such as $H_2SO_4$, HCl or $BF_3$.etherate, citric acid, acetic acid and the like.

Reductions of carbonyls can be carried out with metal hydride reducing agents and reductions of olefins and acetylenes can be carried out by hydrogenation.

Conditions for palladium catalyzed addition/elimination reactions are well-known to the art, and can be carried out with Pd(O) catalysts, or with palladium catalysts that are reduced thereto under the conditions of the reactions, such as Pd(OAc)$_2$, PdCl$_2$, and the like. Copper halide salts can promote the coupling of terminal acetylenes with olefinic iodides. Additional Pd catalysts useful in these reactions are disclosed in U.S. Pat. No. 5,233,059.

Preparation of the bis-THF-containing building blocks 3 and 4 is outlined in FIG. 1. In the early stage, the synthesis follows the approach of S. C. Keinan et al., *J. Amer. Chem. Soc.*, 115, 4891 (1993), who constructed the two carbon longer homolog of lactone 9. Thus, double asymmetric dihydroxylation by the procedure of K. B. Sharpless et al., *J. Org. Chem.*, 57, 2768 (1992), of the E, E-diene 6 (made by the doubly iterative Claisen/Johnson rearrangement of undecanal) provided a crystalline triol lactone that was protected as the acetonide 7 (72%). Tosylation and methanolysis gave epoxide 8 (91%), which underwent Lewis acid catalyzed cyclization to lactone 9 (63%) following hydrolytic workup. Protection of the hydroxyl group as its t-butyldimethylsilyl (TBS) ether and standard processing of the lactone gave the chain-extended allylic alcohol 10 (66%).

This diol was a suitable substrate for Sharpless asymmetric epoxidation, provided that a relatively large amount (50 mol %) of Ti(IV) catalyst was used. The intermediate epoxide spontaneously cyclized to the bis-THF diol 11 (87%, based upon recovered starting material at about 50% conversion). Selective silylation of the primary alcohol as its t-butyldiphenylsilyl (TBDPS) either and tosylation of the single hydroxyl group in 12 (86%) gave 13 (98%). Desilylation of 13 with excess TBAF provided the cyclized epoxy alcohol 14 (88%).

Intermediate 14 contains the same configuration at all stereogenic centers as (+)-asimicin (1): The configuration at [C(24)] is opposite to that required for (+)-bullatacin (2): Thus, compound 14 represents the point of divergence for preparation of subunits 3 and 4. The epoxide in 14 was smoothly pened with TMS—C≡C—Li (2.8 equiv) in the presence of BF$_3$.OEt$_2$, following the rocedures of M. Yamaguchi et al., *Tett. Lett.*, 24, 391 (1983); J. Morris et al., *Tett. Lett.*, 27, 803 (1986) and P. Mohr et al., *Tett. Lett.*, 28, 391 (1987). TMS removal provided the terminal alkyne 3 (70%). Mitsunobu inversion of the carbinol center in 14 required the use of p-nitrobenzoic acid. (S. F. Martin et al., *Tett. Lett.*, 32, 3017 (1991); J. A. Dodge et al., *J. Ore. Chem.*, 59, 234 (1994)). Acetylide opening of the inverted p-nitrobenzoate ester derivative of 14 (2.0 equiv of TMS—C≡C—Li) and methanolysis to remove both the TMS and PNB groups provided the key C(24)-epimeric intermediate 4 (34%).

Figure 2:
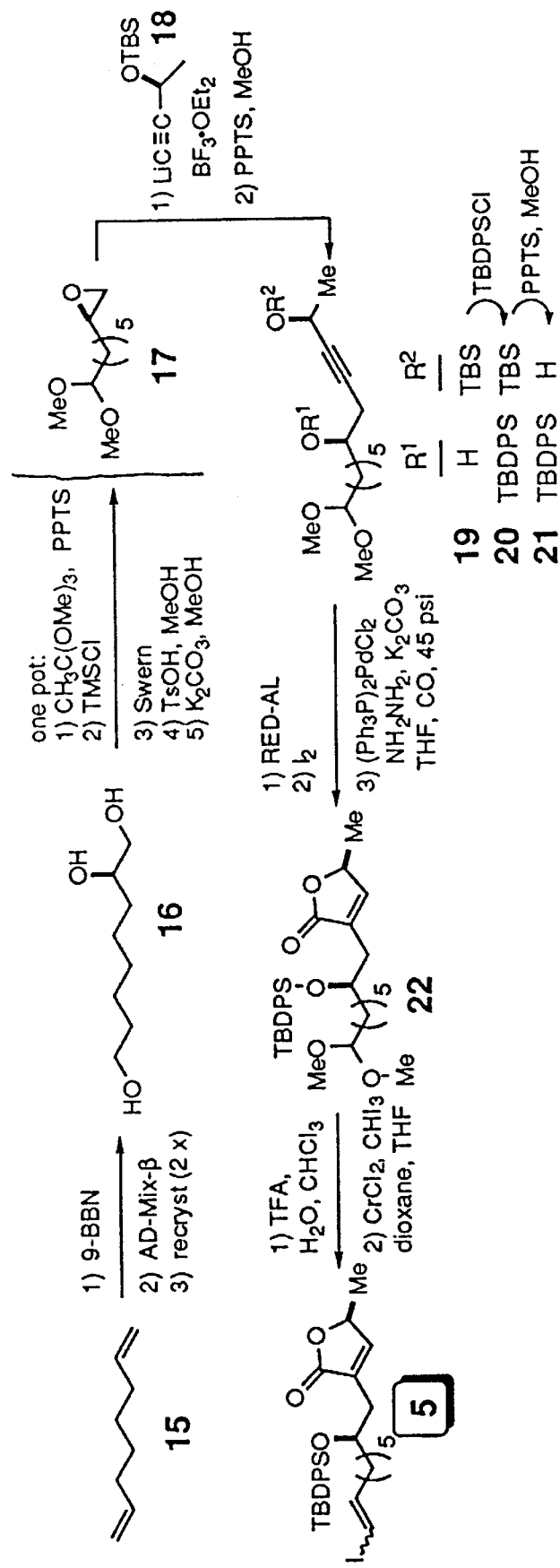

Preparation of the enantiomerically pure butenolide 5 is outlined in FIG. 2, and follows the general route of Hoye et al., *Tett. Lett.*, 35, 7517 (1994). Crystalline triol 16 was produced in about 80% enantiomeric excess (tris-MTPA $^1$H NMR analysis) from 1,7-octadiene (15) by selective hydroboration of one olefin and asymmetric dihydroxylation of the remaining alkene (K. B. Sharpless et al., *J. Org. Chem.*, 57, 2768 (1992)). Recrystallization gave material of high optical purity (tris-MTPA analysis) in 64% overall yield. In an efficient one-pot procedure the triol 16 was processed into the optically pure epoxyacetal 17 (86%). As shown in scheme 1, below, dioxolane i was opened in situ with trimethylsilyl chloride to the chloroacetate ii (or the corresponding TMS ether iii) in accord with the procedures of H. Kolb et al., *Tett. Lett.*, 48, 10515 (1992). The volatile methanol/TMSOMe/HCl/CH$_2$Cl$_2$ mixture was replaced with pure CH$_2$Cl$_2$ and Swem oxidation provided iv. Volatiles were again removed and replaced with methanolic TsOH (cat.) to generate the dimethylacetal v, which gave epoxide 17 simply by addition of excess potassium carbonate.

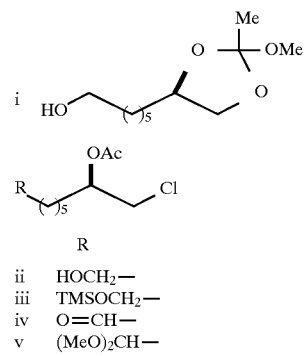

(Scheme 1)

ii  HOCH$_2$—
iii TMSOCH$_2$—
iv O═CH—
v  (MeO)$_2$CH—

Opening of this epoxide (17), with the lithium acetylide 18, derived from optically pure 3-butyn-2-ol, followed by reprotection of a portion of liberated aldehyde gave the homopropargylic alcohol 19 (88%). Silylation of the eventual C(4)

hydroxyl group and selective removal of the TBS ether in 20 produced the propargylic alcohol 21 (80%). REDAL reduction and iodine treatment gave a Z-vinyl iodide that was readily carbonylated under Stille conditions to produce the butenolide 22 (83%) (J. K. Stille et al., *J. Amer. Chem. Soc.*, 102, 4193 (1980)). Hydrolysis of the acetal and generation of the terminal vinyl iodide (about 4:1 E:Z ratio), in accord with the methodology of D. B. Evans et al., *J Amer. Chem. Soc.*, 115, 11446 (1993), completed the preparation of sub-unit 5 (72%).

Figure 3:
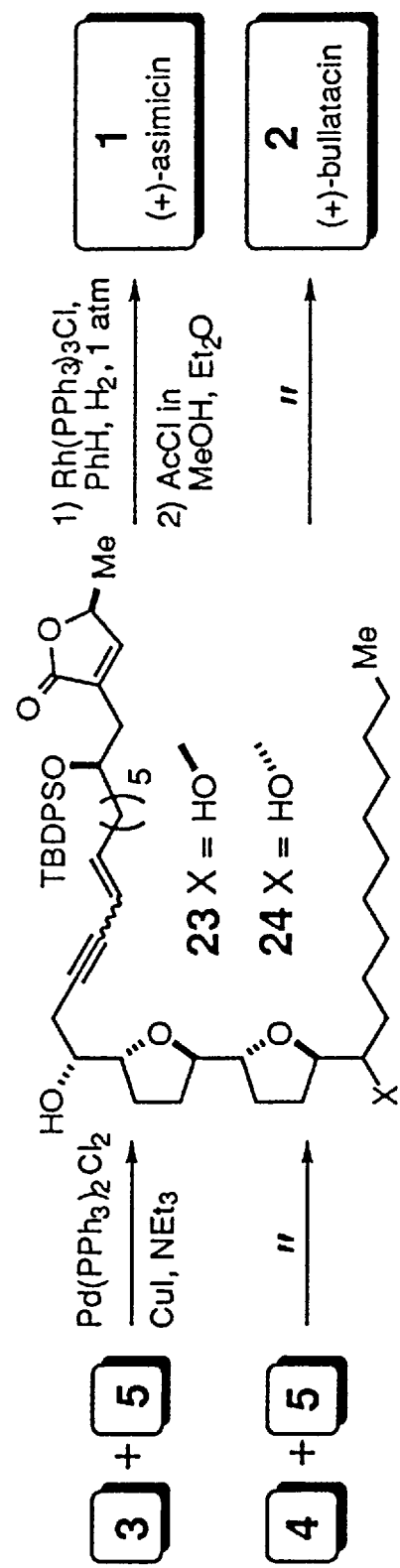

As shown in FIG. 3, Pd°-Catalyzed coupling of alkyne 3 (or 4) with vinyl iodide 5 gave the enyne 23 (or 24) in 79% (or 82%) yield. Enyne 23 was hydrogenated with Wilkinson's catalyst in carefully deoxygenated benzene and desilylated to give (+)-asimicin (1, mp 68°–68.5° C., 75%). (B. M. Trost et al., *J. Amer. Chem. Soc.*, 116, 4985 (1994)); B. M. Trost et al., *J. Amer. Chem. Soc.*, 116, 7459 (1994). Similar treatment of 24 provided (+)-bullatacin (2, mp 68.5°–69° C., 74%). Each of the synthetic samples gave $^1$H and $^{13}$C NMR and HRMS spectra consistent with those from the natural material; the specific rotations for 1 and 2 were $[\alpha]_D^{RT}=+14.7°$ (c=0.31, CHCl$_3$) and $[\alpha]_D^{RT}=+12.8°$ (c=0.26, CHCl$_3$, lit.[5] $[\alpha]_{578}^{25}=+13.0°$ (c=0.004, CHCl$_3$)], respectively. This synthesis represents the most efficient to date of the structurally complex, bis-tetrahydrofuranyl acetogenins, and is readily adaptable to generally prepare compounds of formulas I–XV.

The invention will be fuirther described by reference for to the following detailed examples.

EXAMPLE 1

(+)-Tridec-1-en-3-ol (i-a)

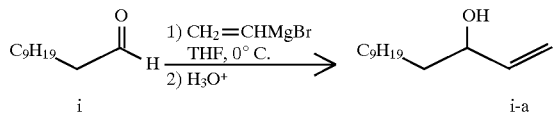

To a solution of vinyl magnesium bromide in tetrahydrofuiran (1M, 82.0 mL) at 0° C. was added a solution of undecanal i (7.00 g, 41.1 mmol) in tetrahydrofuiran (25 mnL) in about 10 min. After 6 h at 0° C., saturated ammonium chloride solution (50 mL) was added. The two layers were separated. The water layer was extracted with ether (2×50 mL). The combined organic solutions were dried over anhydrous magnesium sulfate, filtered, and concentrated. The residue was purified by flash chromatography (10% ethyl acetate in hexane) to give 7.94 g (98%) of i-a as a colorless oil: IR (neat) 3409, 3079, 1644, and 1463 cm$^{-1}$; $^1$H NMR (CDCl$_3$, 300 MHz) δ 5.80 (ddd, 1 H, J=6.3, 10.7, and 17.2 Hz, CH=CH$_2$), 5.55 (dd, 1 H, J=17.2 and 1.4 Hz, CH=CH$_2$), 5.05 (dd, 1 H, J=10.7 and 1.4 Hz, CH=CH$_2$), 3.99 (q, 1 H, J=6.2 Hz, CHOH), 2.58 (br s, 1 H, OH), 1.46–1.22 [m, 18 H, C(4–12)H$_2$ ], and 0.83 (t, J=6.4 Hz, CH$_2$CH$_3$); $^{13}$C NMR (CDCl$_3$, 75.5 MHz) δ 141.61, 114.50, 73.33, 37.24, 32.12, 29.83, 29.55, 25.57, 22.87, and 14.26.

EXAMPLE 2

Ethyl (E)-Pentadec-4-enoate (i-b)

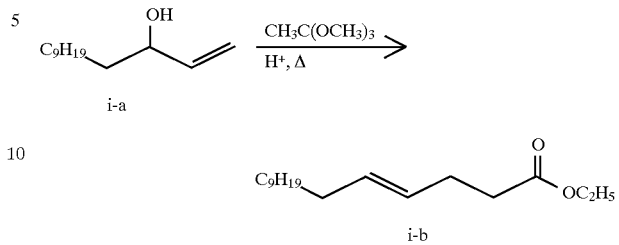

A 100 mL, one-necked, round-bottomed flask containing a magnetic stirring bar was fitted with a Claisen adapter, two thermometers, and a receiving flask. To the flask was added 7.78 g (39.3 mmol) of i-a, 43 mL of ethyl orthoacetate (distilled immediately before use), and 0.12 mL of propionic acid. The mixture was heated with stirring to keep the temperature above the liquid at 138°~142° C. Heating was continued until ethanol no longer distilled from the reaction flask (approximately 1 h). The reaction mixture was allowed to cool to room temperature, and the excess orthoester and propionic acid were removed by distillation under reduced pressure. Flash chromatography (5% ethyl acetate in hexane) of the light yellow oil gave 10.32 g (98%) of i-b as a colorless oil: IR (neat) 2925, 1738, 1462, 1372, 1243, and 1174 cm$^{-1}$; $^1$H NMR (CDCl$_3$, 300 MHz) δ 5.39 (m, 2 H, CH=CH), 4.09 (q, J=7.2 Hz, 2 H, OCH$_2$), 2.31 [m, 4 H, C(2, 3)H$_2$], 1.93 [ddd, J=6.6, 6.6, and 6.6 Hz, 2 H, C(6)H$_2$], 1.23 [m, 19 H, C(7–14)H$_2$ and OCH$_2$CH$_3$], and 0.86 (t, J=7.2 Hz, 3 H, CH$_3$); $^{13}$C NMR (CDCl$_3$, 75.5 MH) δ 173.36, 131.97, 128.03, 60.31, 34.56, 32.64, 32.04, 29.76, 29.65, 29.59, 29.47, 29.26, 28.08, 22.81, 14.37, and 14.22.

EXAMPLE 3

(E)-Pentadec-4-enal (i-c)

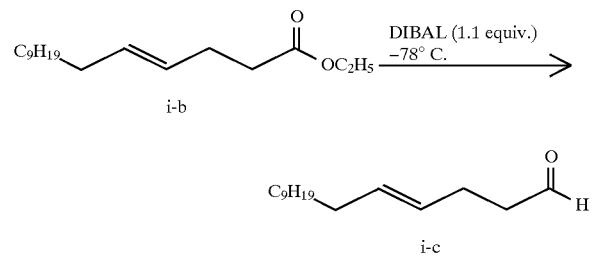

To a solution of i-b (10.21 g, 38.1 nunol) in methylene chloride (80 mL) was added DIBAL-H (7.5 mL, 41.9 mmol) very slowly (about 30 min) at −78° C. The solution was stirred at −78° C. for 1 h. Methanol (10 mL) was added. After 10 min, the solution was allowed to warm to room temperature, and saturated ammonium chloride (50 mL) was added. The solution was stirred at room temperature for 2 h and then filtered. The two layers of the filtrate were separated. The water layer was extracted with methylene chloride (2×50 mL). The combined organic solutions were dried over anhydrous magnesium sulfate, filtered, and concentrated. Flash chromatography (5% ethyl acetate in hexane) of the residue afforded 7.5 g (88%) of the aldehyde i-c as a colorless oil: IR (neat) 2854, 2714, 1729, and 1463 cm$^{-1}$; $^1$H NMR (CDCl$_3$, 300 MHz) δ 9.70 (t, J=0.8 Hz, 1 H, CH=O), 5.38 (m, 2 H, CH=CH, 2.41 (dt, J=0.8 and 7.0 Hz, 2 H, CH$_2$CH=O), 2.28 [dt, J=6.5 and 6.5 Hz, 2 H, C(3)H$_2$], 1.92 [dt, J=6.4 and 6.4 Hz, 2 H, C(6)H$_2$], 1.21 [m, 16 H, C(7–14)H$_2$], and 0.85 (t, J=6.3 Hz 3 H, CH$_3$); $^{13}$C NMR (CDCl$_3$, 75.5 MHz) δ 201.77, 131.81, 127.39, 43.29, 32.24, 31.67, 29.39, 29.26, 29.18, 29.10, 28.91, 27.05, 24.95, 22.43, and 13.81. Anal. Calcd for C$_{15}$H$_{28}$O: C, 80.29%; H, 12.58%. Found: C, 80.37%; H, 12.30%.

EXAMPLE 4

(+)-(E)-Hentadeca-1,6-dien-3-ol (i-d)

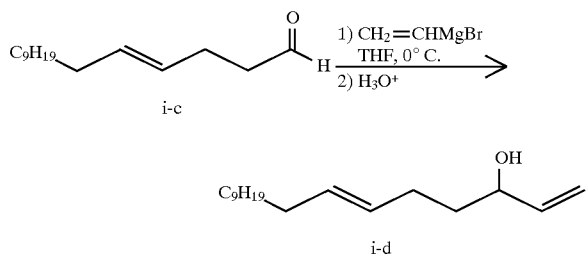

This compound was prepared by the same procedure as compound i-a. Chromatography (8% ethyl acetate in hexane) afforded a 98% yield of i-d as a colorless oil: IR (neat) 3406, 2924, 1639, and 1461 cm$^{-1}$; $^1$H NMR (CDCl$_3$, 300 MHz) δ 5.84 (ddd, J=4.1, 10.4, and 17.2 Hz, 1 H, CH=CH$_2$), 5.40 (m, 2 H, CH=CH), 5.09 (ddd, J=17.2, 1.5, and 1.5 Hz, 1 H, CH=CH$_a$H$_b$), 5.05 (dt, J=10.4 1.5, and 1.5 Hz, 1 H, CH=CH$_a$H$_b$), 4.07 (m, 1 H, CHOH), 2.05 (m, 2 H, CH$_2$), 1.94 (m, 2 H, CH$_2$), 1.88 (br s, 1 H, OH), 1.58 [m, 2 H, C(8)H$_2$, 1.24 [m, 16 H, C(9–17)H$_2$], and 0.86 (t, J=6.4 Hz, 3 H, CH$_3$); $^{13}$C NMR (CDCl$_3$, 75.5 MHz) δ 141.41, 131.45, 129.60, 114.66, 72.87, 37.02, 32.80, 32.14, 29.86, 29.80, 29.75, 29.57, 29.41, 28.81, 22.90, and 14.30. Anal. Calcd for C$_{17}$H$_{32}$O: C, 80.89%; H, 12.78%. Found: C, 81.06%; H, 12.60%.

EXAMPLE 5

Ethyl (4E,7E)-Nonadeca-4,8-dienoate (6)

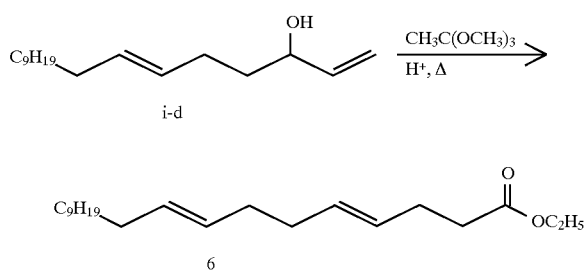

This compound was prepared by the same procedure as compound i-b. Flash chromatography (3% ethyl acetate in hexane) of the crude product gave 94% of 6 as a colorless oil: IR (neat) 1740, 1462, 1148 and 967 cm$^{-1}$; $^1$H NMR (CDCl$_3$, 300 MHz) δ 5.37 (m, 4 H, CH=), 4.09 (q, J=7.1 Hz, 2 H, OCH$_2$), 2.28 [m, 4 H, C(2, 3)H$_2$], 1.94 [m, 4 H, C(6, 7)H$_2$], 1.91 [m, 2 H, C(10)H$_2$], 1.30–1.16 [m, 19 H, C(11–18)H$_2$ and CH$_3$CH$_2$O], and 0.85 (t, J=6.4 Hz, 3 H, CH$_3$CH$_2$); $^{13}$C NMR (CDCl$_3$, 75.5 MHz) δ 172.81, 130.86, 130.56, 129.16, 128.01, 59.85, 34.11, 32.36, 32.30, 32.26, 31.64, 29.37, 29.25, 29.07, 28.89, 27.66, 22.40, 13.96, and 13.76. Anal. Calcd for C$_{21}$H$_{38}$O$_2$: C, 78.20%; H, 11.88%. Found: C, 78.23%; H, 12.00%.

EXAMPLE 6

(−)-{5R-[5R*(1R*,4R*,5R*)]}-Dihydro-5-(1,4,5-trihydroxytentadecyl)-2(3H-furanone (6-a)

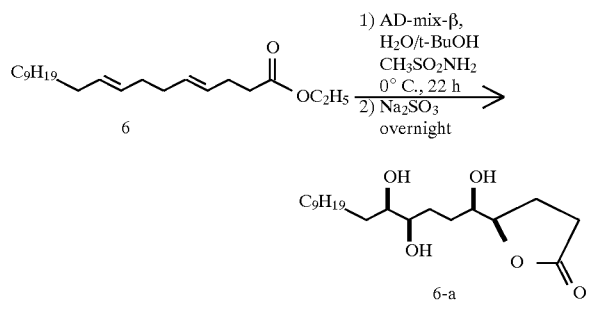

A 250-mL round-bottomed flask, equipped with a magnetic stirrer, was charged with 101 mL of t-butyl alcohol, 101 mL of water and 28.26 g of AD-mix-b. Stirring at room temperature produced two clear phases, the lower aqueous phase appears bright yellow. Methylsulfonyl amide (1.92 g, 20.18 mmol) was added. The mixture was cooled to 0° C. whereupon some of the dissolved salts precipitated. Compound 6 (3.25 g, 10.09 mmol) was added at once, and the heterogeneous slurry was stirred vigorously at 0° C. for 22 h. While the mixture was stirred at 0° C., sodium sulfite was added. The reaction mixture was allowed to warm to room temperature and stirred overnight. Ethyl acetate (200 mL) was added. After the separation of the two layers, the aqueous layer was ftrther extracted with ethyl acetate (3×100 mL). The combined organic solutions were washed with 2N potassium hydroxide (100 mL), dried over anhydrous magnesium sulfate, filtered, and concentrated. The crude solid was recrystallized from ethyl acetate to give 2.55 g (73%) of the desired product: mp 99°–100° C.; [α]$_D^{RT=}$−3.2°; IR (KBr pellet) 3391, 2850, 1732, 1471, 1203, and 1052 cm$^{-1}$; $^1$H NMR (300 MHz, CDCl$_3$) δ 4.42 (ddd, J=11.2, 11.2, and 4.1 Hz, 1 H, CHOC=O), 3.60 (ddd, J=4.1, 4.1, and 4.1 Hz, 1 H, CHOHCHOC=O), 3.40 (m, 2 H, CHOH), 3.14 (br s, 3 H, OH, 2.68–2.43 (m, 2 H, CH$_2$C=O), 2.26–2.08 (m, 2 H, CH$_2$CH$_2$C=O) 1.71–1.62 (m, 4 H, CHOHCH$_2$CH$_2$CHOH), 1.46 (m, 2 H, CH$_2$CH$_2$CH$_2$CHOH), 1.25 (m, 16 H, CH$_2$) and 0.86 (t, J=6.4 Hz, 3 H, CH$_2$CH$_3$); $^{13}$C NMR (CDCl$_3$, 75.5 MHz) 177.92, 83.21, 74.59, 74.21, 73.31, 33.39, 31.75, 29.75, 29.50, 29.19, 28.51, 25.61, 23.72, 22.52, and 13.94. Anal. Calcd for C$_{19}$H$_{36}$O$_5$: C, 66.25; H, 10.53. Found: C, 66.31; H, 10.38.

EXAMPLE 7

(+)-{4R-[4α[R*(R*)],5β]}-5-[3-(5-Decyl-2,2-dimethyl-1,3-dioxolan-4-yl)-1-hydroxypropyl]dihydro-2(3H)-furanone (7)

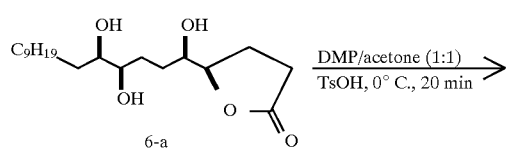

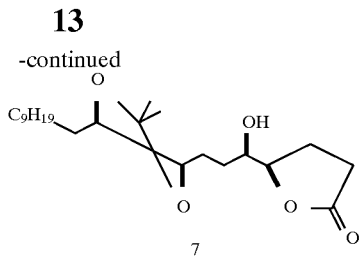

To a solution of 6-a (4.50 g, 13.08 mmol) in 40 nil of 2,2-dimethoxypropane and acetone (1:1), p-toluenesulfonic acid (0.37 g, 1.96 nmmol) was added at 0° C. After stirred at 0° C. for 20 min, solid sodium bicarbonate was added portion wise until no more gas evolved. The solvent was removed by evaporation under reduced pressure. The residue was transferred onto ~40 g of silica gel in a funnel and eluted with ethyl acetate/hexane (1:1) to give 4.92 g (98%) of 7 as a colorless oil: $[\alpha]_D^{RT}=+9.0°$ (c=2.19, CHCl$_3$); IR (neat) 3446, 2855, 1775, 1458, 1369, and 1241 cm$^{-1}$; $^1$H NMR (CDCl$_3$, 300 MHz) δ 4.36 (ddd, J=7.0, 7.0, and 4.0 Hz, 1 H, CHOC=O), 3.59–3.52 (m, 3 H, CHOH, CHOCCHOC), 3.24 (br s, 1 H, OH), 2.59–2.36 (m, 2 H, CH$_2$C=O), 2.19–2.06 (m, 2 H, CH$_2$CH$_2$C=O), 1.71–1.53 (m, 4 H, CHOHCH$_2$CH$_2$CHOC), 1.42–1.34 (m, 2 H, CH$_2$CH$_2$CH$_2$CHOC), 1.29 (s, 6 H, CH$_3$C), 1.18 (m, 16 H, CH$_2$), and 0.80 (t, J=6.4 Hz, 3 H, CH$_2$CH$_3$); $^{13}$C NMR (CDCl$_3$, 75.5 MHz) δ 177.31, 107.81, 82.81, 80.78, 80.48, 73.01, 32.51, 31.67, 29.59, 29.52, 29.36, 29.28, 29.08, 28.92, 28.37, 27.10, 27.03, 25.85, 23.79, 22.44, and 13.88. Anal. Calcd for C$_{22}$H$_{40}$O$_5$: C, 68.71%; H, 10.48%. Found: C, 68.73%; H, 10.26%.

EXAMPLE 8

(+)-{4R-[4α[R*(R*)],5β-]}-5-3-(5-Decyl-2,2-dimethyl-1,3-dioxolan-4-yl)-1-[[(4-methylphenyl)sulfonyl]oxy]propyl]dihydro-2(3H)-furan one (7-a)

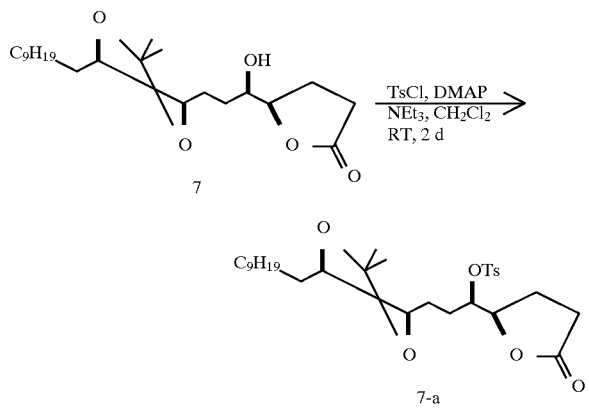

To a solution of 7 (4.87 g, 12.68 mmol) in methylene chloride (30 mL) were added sequentially triethylamine (4.41 mnL, 12.18 mmol), 4-(N,N-dimethylamino)pyridine (0.32 g, 20 mol %), and p-toluenesulfonyl chloride (3.61 g, 7.30 mmol) . The resulting solution was stirred at room temperature for 2 days. Brine (100 mL) was added. The two layers were separated. The aqueous layer was extracted with ethyl acetate (3×100 mL). The combined organic solutions were dried over anhydrous magnesium sulfate, filtered and concentrated. Flash chromatography (40% ethyl acetate in hexane) of the residue gave 6.69 g (98%) of 7-a as a light yellow oil: $[\alpha]_D^{RT}=+9.0°$ (c=2.95, CHCl$_3$); IR (neat) 2984, 1785, 1598, 1458, 1368, and 1177 cm$^{-1}$; $^1$H NMR (CDCl$_3$, 300 MHz) δ 7.75 (d, J=8.1 Hz, 2H, ArH), 7.30 (d, J=8.1 Hz, 2 H, ArH), 4.74 (ddd, J=6.7, 6.7, and 3.2 Hz, 1 H, CHOTs or CHOC=O), 4.62 (ddd, J=6.0, 6.0, and 3.2 Hz, 1 H, CHOTs or CHOC=O), 3.42 (m, 2 H, CHOCCHOC), 2.51–2.45 (m, 2 H, CH$_2$C=O), 2.41 (s, 3 H, ArCH$_3$,.), 2.35–2.12 (m, 2 H, CH$_2$CH$_2$C=O), 1.84–1.77 (m, 2 H, COCHCH$_2$CH$_2$CHOTs), 1.52–1.47 (m, 4 H, COCHCH$_2$CH$_2$CHOTs and CH$_2$CH$_2$CH$_2$CHOC), 1.27 (s, 3 H, CH$_3$C), 1.23 (s, 3 H, CH$_3$C), 1.18 (m, 16 H, CH$_2$), and 0.83 (t, J=6.3 Hz, CH$_2$CH$_3$). $^{13}$C NMR (CDCl$_3$, 75.5 MHz) δ 176.42, 145.20, 133.90, 129.94, 127.81, 108.02, 82.56, 80.95, 80.31, 78.76, 32.74, 31.94, 29.81, 29.64, 29.57, 29.36, 28.10, 27.82, 27.37, 27.29, 26.13, 23.65, 22.72, 21.70, and 14.17. Anal. Calcd for C$_{29}$H$_{46}$O$_7$: C, 64.65%; H, 8.61%. Found: C, 64.37%; H, 8.77%.

EXAMPLE9

Methyl (+)-{4R-[4α(2R*,3S*),5β]}-3-[2-(5-Decyl-2,2-dimethyl-1,3-dioxolan-4-yl)ethyl] oxiranepropanoate (8)

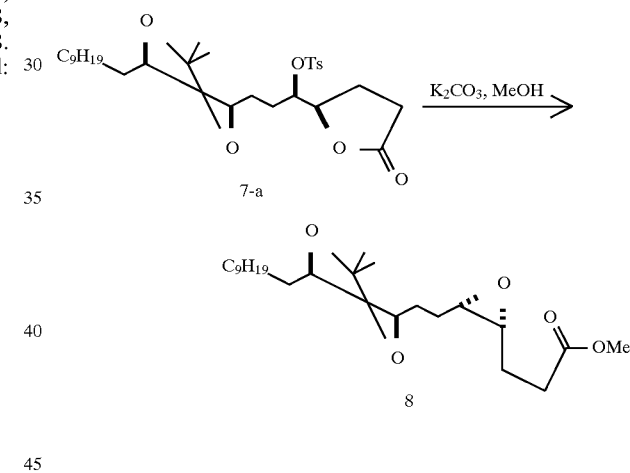

To a solution of 7-a (6.69 g, 12.43 mmol) in methanol (30 mL) was added potassium carbonate (1.72 g, 12.43 mmol). After the reaction mixture was stirred at room temperature for 2.5 h, ethyl acetate (250 mL) was added. The solution was washed with water (2×50 mL), dried with anhydrous magnesium sulfate, filtered, and concentrated. Flash chromatography (30% ethyl acetate in hexane) of the residue gave 4.55 g (92%) of 8 as a colorless oil: $[\alpha]_D^{RT}=+20.3°$ (c=4.02, CHCl$_3$); IR (neat) 2927, 1742, 1457, 1439, 3368, and 1172 cm$^{-1}$; $^1$H NMR (CDCl$_3$, 300 MHz) δ 3.57 (s, 3 H, OCH$_3$), 3.49 (m, 2 H, CHOCCHOC), 2.85 (dt, J=9.4 Hz and 4.7 Hz, 2 H, CHOCH, CHOCH, 2.45–2.30 (m, 2 H, CH$_2$C=O), 1.66–1.26 (m, 8 H, CH$_2$CH$_2$C=O, CHOCH$_2$CH$_2$CHOC, and CH$_2$CH$_2$CH$_2$CHOC), 1.26 (s, 6 H, CCH$_3$), 1.01 (m, 16 H, CH$_2$), and 0.77 (t, J=6.3 Hz, 3 H, CH$_2$CH$_3$); $^{13}$C NMR (CDCl$_3$, 75.5 MHz) δ 173.12, 108.00, 81.10, 80.81, 57.23, 56.07, 51.61, 32.95, 31.95, 30.96, 30.16, 29.79, 29.63, 29.54, 29.36, 27.35, 26.14, 25.04, 23.44, 22.71, and 14.12. Anal. Calcd for C$_{23}$H$_{42}$O$_5$: C, 69.31%; H, 10.62%. Found: C, 69.08%; H, 10.67%.

EXAMPLE 10

(−)-{2'R-[2'α(R*),5'β(R*)]}-Hexahydro-5'-(1-hydroxyundecyl)-2,2'-bifuran-5(2H)-one (9)

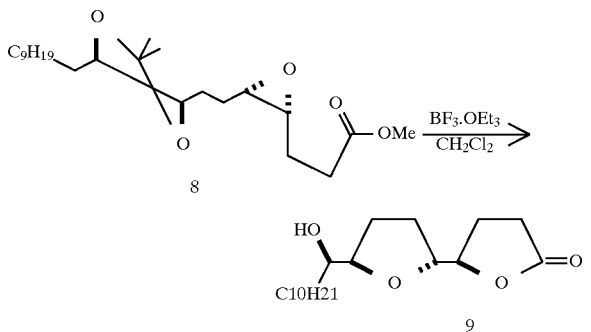

To a solution of 8 (4.55 g, 11.44 mmol) in methylene chloride (30 mL) was added borontrifluoride etherate (0.28 mL, 20 mmol %) at room temperature. The resulting solution was stirred at room temperature for 3 h. Water (50 mL) was added. After the solution was stirred at room temperature vigorously for 1 h, the two layers were separated. The aqueous layer was extracted with ethyl acetate (3×30 mL). The combined organic solutions were dried over anhydrous magnesium sulfate, filtered and concentrated. The crude solid was recrystallized from ethyl acetate to give 2.55 (63%) g of 9 as a white solid: mp 92.5°–93.5° C.; $[\alpha]_D^{RT}$= −4.7° (c=1.44, CHCl$_3$); IR (neat) 3441, 1768, 1740, 1467, 1235, and 1077 cm$^{-1}$; $^1$H NMR (CDCl$_3$, 300 MHz) δ 4.42 (ddd, J=7.9, 5.2, and 3.0 Hz, 1 H, CHOC=O), 4.02 (ddd, J=7.5, 7.5, and 3.0 Hz, 1 H, CHOCHOC=O), 3.79 (ddd, J=8.0, 5.8, and 5.8 Hz, 1 H, CHOCHOH), 3.33 (ddd, J=5.4, 5.4, and 5.4 Hz, 1 H, CHOH), 2.54 (ddd, J=6.9, 9.9, and 17.0 Hz, 1 H, CHaH$_b$C=O), 2.42 (ddd, J=6.6, 9.7, and 17.5 Hz, 1 H, CH$_a$H$_b$C=O), 2.28–2.12 (m, 3 H, CH$_2$CHOC=O and OH), 2.02–1.63 (m, 4 H, CHOCH$_2$CH$_2$CHO), 1.37–1.33 (m, 2 H, CH$_2$CHOH), 1.37–1.21 (m, 16 H, CH$_2$), and 0.83 (t, J=6.3 Hz, CH$_2$CH$_3$); $^{13}$C NMR (CDCl$_3$, 75.5 MHz) δ 177.54, 83.62, 81.41, 80.89, 73.74, 33.82, 32.01, 29.77, 29.71, 29.43, 28.34, 28.31, 28.22, 25.70, 24.23, 22.18, and 14.22. Anal. Calcd for C$_{19}$H$_{34}$O$_4$: C, 69.90%; H, 10.50%. Found: C, 70.04%; H, 10.46%.

EXAMPLE 11

(−)-{2'R-[2'α(R*),5'β(R*)]}-Hexahydro-5'-{1-[(1,1-dimethylethyl)dimethylsilyloxy]undecyl}-2,2'-bifuran-5(2H)-one (9-a)

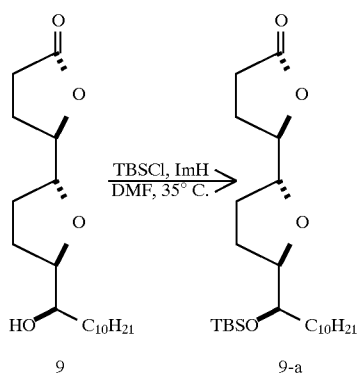

To a solution of 9 (1.72 g, 5.28 mmol), in N,N-dimethyl formamide (3 mL), were added t-butyldimethylsilyl chloride (1.12 g, 7.39 mmol) and imidazole (0.91 g, 13.2 nmmol) sequentially. After the resulting solution was heated to 35° C. for 18 h, water (10 mL) and ether (10 mL) were added. The two layers were separated. The aqueous layer was extracted with ether (4×10 mL). The combined organic solutions were dried over anhydrous magnesium sulfate, filtered and concentrated. Flash chromatography (25% ethyl acetate in hexane) of the residue gave 2.02 g (87%) of 9-a as a colorless oil: $[\alpha]_D^{RT}$=−0.96° (c=2.00, CHCl$_3$); IR (neat) 2855, 1781, 1463, 1252, 1168, 835, and 775 cm$^{-1}$; $^1$H NMR (CDCl$_3$, 300 MHz) δ 4.34 (ddd, J=7.8, 5.9, and 2.5 Hz, 1 H, CHOC=O), 3.92 (ddd, J=6.8, 6.8, and 2.5 Hz, 1 H, CHOCHOC=O), 3.82 (ddd, J=7.6, 5.5, and 5.5 Hz, 1 H, CHOCHOTBS), 3.43 (ddd, J=5.5, 5.5, and 5.5 Hz, 1 H, CHOTBS), 2.50 (ddd, J=17.0, 10.0, and 7.2 Hz, 1 H, CH$_a$H$_b$C=O), 2.30 (ddd, J=17.0, 9.5, and 6.7 Hz, 1 H, CH$_a$H$_b$C=O), 2.11 (m, 2 H, CH$_2$CH$_2$C=O), 1.87 (m, 4 H, CHOCH$_2$CH$_2$CHO), 1.58 (m, 2 H, CH$_2$CHOTBS), 1.57–1.15 (m, 16 H, CH$_2$), 0.83–0.78 [m, 12 H, SiC(CH$_3$)$_3$ and CH$_2$CH$_3$)], −0.04 (s, 3 H, SiCH$_3$), and −0.05 (s, 3 H, SiCH$_3$); $^{13}$C NMR (CDCl$_3$, 75.5 MHz) δ 177.52, 82.91, 81.34, 80.72, 74.94, 33.34, 31.97, 29.94, 29.66, 29.40, 28.76, 28.21, 27.98, 27.62, 25.99,−25.43, 24.66, 22.74, 18.23, 14.16, −4.25, and −4.50. Anal. Calcd for C$_{25}$H$_{48}$O$_4$Si: C, 68.13%; H, 10.98%. Found: C, 68.28%; H, 10.89%.

EXAMPLE 12

Lactols 9-b

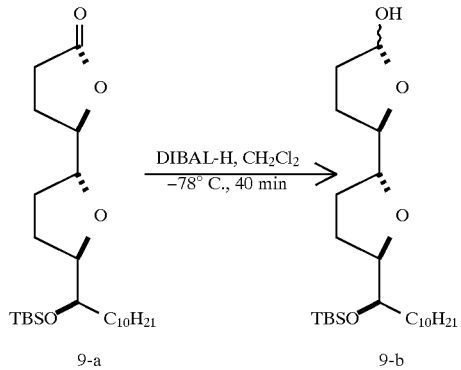

To a solution of 9-a (2.02 g, 4.59 mmol) in methylene chloride (50 mL) at −78° C., was added DIBAL-H (0.90 mL, 5.05 mmol). After the resulting solution was stirred at −78° C. for 40 min, methanol (5 mL) was added. The solution was allowed to warm to room temperature after 5 min. Saturated anmmonium chloride (50 mL) was added. After stirred at room temperature for 2 h, the mixture was filtered. The solid was washed with methylene chloride (3×30 mL). The two layers of the. filtrate were separated. The organic phase was dried over anhydrous magnesium sulfate, filtered, and concentrated. Flash chromatography (20% ethyl acetate in hexane) of the residue gave 1.90 g (87%) of 9-b as a colorless, approximately 1:1 mixture of epimer: IR (neat) 3418,1463, 1252, 1100, and 775 cm$^{-1}$, $^1$H NMR (CDCl$_3$, 300 MHz) δ 5.50 br s, ~1/2 H, (OCHOH)$_a$], 5.31 [br dd, J=9 and 4 Hz, ~1/2 H, (OCHOH)$_b$], 4.20 [d, J=8.5 Hz, (OH$_b$], 4.10–4.00 (m, 1 H), 3.94–3.79 (m, 2 H), 3.55–3.49 (m, 1 H), 2.09–1.73 (m, 5 H), 1.71–1.54 (m, 3 H), 1.44–1.18 (m, 18 H), 0.8 [br s, 12 H, $SiC(CH_3)_3$ and $CH_2CH_3$)], and −0.01, −0.03+, −0.03, −0.04 (4 S's, $CH_3Si$); $^{13}C$ NMR ($CDCl_3$, 75.5 MHz) δ 99.04, 98.66, 82.73, 82.38, 81.47, 81.30, 80.84, 80.54, 75.05, 74.88, 34.81, 33.28, 33.10, 32.63, 32.08, 30.12, 30.09, 29.78, 29.52, 28.95, 28.56, 28.14, 27.31, 26.09, 25.98, 25.40, 25.19, 22.85, 18.33, 18.27, 14.35, 14.28, −4.11, −4.39, and −4.46. HRMS (CI, $NH_3$ as ionizing gas) calcd for $C_{25}H_{54}NO_4Si$ $(M+NH_4^+)$: 460.3822. found: 460.3804.

EXAMPLE 13

Enoate 9-c

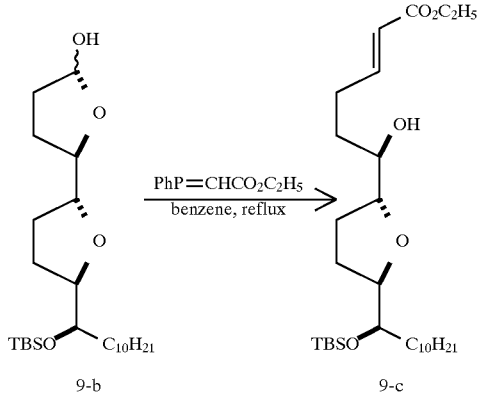

9-b    9-c

To a solution of 9-b (1.90 g, 4.31 mmol) in benzene (10 mL), was added (carboethoxymethylene) triphenylphosphorane (2.24 g, 6.46 mmol). The mixture was heated to reflux for 1.5 h. The solvent was removed by evaporation under reduced pressure. The residue was dissolved in a small amount of ethyl acetate, and transferred into a funnel containing a bed of silica gel and eluted with 20% ethyl acetate in hexane. After concentrated, the residue was chromatographed (16% ethyl acetate in hexane) to give 2.12 g (96%) of 9-c as a colorless oil: $[α]_D^{RT}$=+10.67° (c=1.57, $CHCl_3$); IR (neat) 3496, 1722, 1654, 1464, 1256, and 1046 cm$^{-1}$; $^1H$ NMR ($CDCl_3$, 300 MHz) δ 6.93 (dt, J=15.6 and 7.6 Hz, 1 H, CH=CHCO), 5.79 (d, J=15.6 Hz, 1 H, CCH=CHCO), 4.12 (q, J=7.1 Hz, 2 H, $OCH_2CH_3$), 3.81 (ddd, J=6.6, 6.6, and 6.6 Hz, 1 H, from among C HOCHOH, CHOCHOH, and CHCHOTBS), 3.72 (ddd, J=6.3, 6.3, and 6.3 Hz, 1 H, from among CHOCHOH, CHOCHOH, and CHCHOTBS), 3.51 (m, 1 H, from among CHOCHOH, CHOCHOH, and CHCHOTBS), 3.34 (m, 1 H, CHOTBS), 2.41–2.23 (m, 3 H, $CH_2$CH= and OH), 1.88 (m, 2 H, $CH_2CH_2CH$=), 1.64–1.22 (m, 28 H, $CH_2$ and $OCH_2CH_3$), 0.84–0.76 [m, 12 H, $SiC(CH_3)_3$ and $CH_2CH_3$], 0.03 (s, 3 H, $SiCH_3$), and 0.01 (s, 3 H, $SiCH_3$). $^{13}C$ NMR ($CDCl_3$, 75.5 MHz) δ 166.55, 148.65, 121.56, 82.31, 82.22, 75.17, 73.06, 60.04, 33.17, 31.83, 29.78, 29.53, 29.27, 28.47, 28.34, 28.25, 25.88, 25.32, 22.61, 18.19, 14.20, 14.04, −4.20, and −4.63. Anal. Calcd for $C_{29}H_{56}O_5Si$: C, 67.92%; H, 11.01%. Found: C, 68.12%; H, 10.85%.

EXAMPLE 14

Allyl alcohol 10

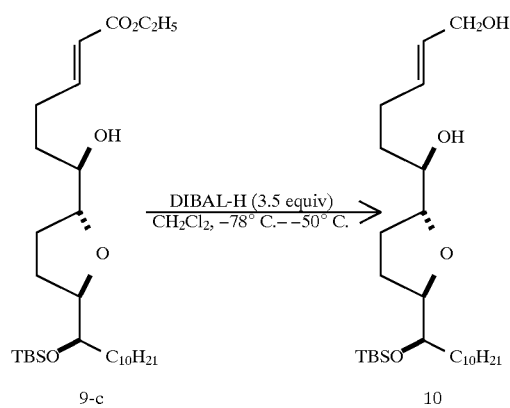

9-c    10

To a solution of 9-c (2.12 g, 4.13 mmol) in methylene chloride (30 mL) was added DIBAL-H (2.58 mL, 14.45 mmol) at −78° C. After 5 min, the solution was armed to −50° C. After 1 h, the reaction mixture was quenched with methanol (5 mL) and warmed to room temperature. Saturated ammonium chloride (20 mL) was added. After stirred at room temperature for 2 h, the solid was removed by filtration. The two layers of the filtrate were separated. The organic solution was dried over anhydrous magnesium sulfate, filtered, and concentrated. Flash chromatography (35% ethyl acetate in hexane) of the residue gave 1.77 g (91%) of 10 as a colorless oil: $[α]_D^{Rt}$=+16.03° (c=1.88, $CHCl_3$); IR (neat) 3401, 1464, 1252, 1088, and 835 cm$^{-1}$; $^1H$ NMR ($CDCl_3$, 300 MHz) 6 5.63 (ddd, J=15.3, 4.8, and 4.8 Hz, 1 H, CH=$CHCH_2OH$), 5.57 (ddd, J=15.3, 5.5, and 5.4 Hz, 1 H, CH=$CHCH_2OH$), 4.99 (d, J=5.3 Hz, 2 H, $CH_2OH$), 3.80 (ddd, J=6.4, 6.4, and 6.4 Hz, 1 H, CHOCHOH), 3.71 (ddd, J=6.3, 6.3, and 6.3 Hz, 1 H, CHOCHOTBS), 3.49 (m, 1 H, CHOTBS or CHOH), 3.33 (ddd, J=6.4, 6.4, and 6.4 Hz, 1 H, CHOH or CHOTBS), 2.51 (br s, 2 H, OH, 2.22–2.07 (m, 2 H, $CH_2CH$=), 1.97–1.85 (m, 2 H, $CH_2CH_2CH$= or $CHOCH_2CH_2$), 1.61–1.49 (m, 2 H, $CH_2CH_2CH$= or $CHOCH_2CH_2$), 1.47–1.13 (m, 18 H, $CH_2$), 0.90–0.77 (m, 12 H, $SiC(CH_3)_3$ and $CH_2CH_3$), 0.01 (s, 3 H, $SiCH_3$), and −0.00 (s, 3 H, $SiCH_3$). $^{13}C$ NMR ($CDCl_3$, 75.5 MHz) δ 132.08, 129.43, 82.25, 82.17, 75.13, 73.2 4, 63.25, 33.06, 32.80, 31.77, 29.73, 29.47, 29.21, 28.40, 28.21, 25.83, 25.28, 22.55, 18.13, 13.98, −4.25, and −4.71. Anal. Calcd for $C_{27}H_{54}O_{4Si}$: C, 68.85%; H, 11.56%. Found: C, 68.76%; H, 11.30%.

EXAMPLE 15

(+)-{2R-{2β[2'R*,5'R*(S*)],5α(R*)}}-α-Decyloctahydro-α'-hydroxymethyl)-2,2'-bifuran-5,5'-dimethanol-α-{[(1,1-dimethylethyl)dimethyl]silylether} (11)

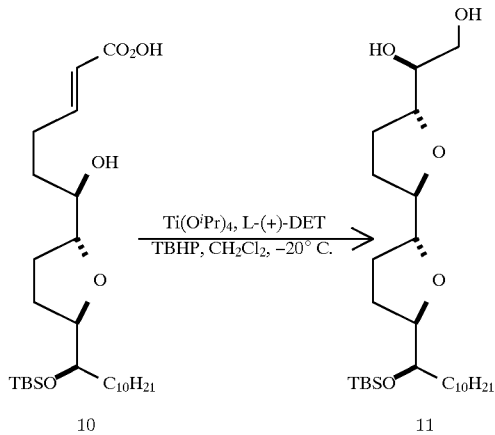

EXAMPLE 16

(+)-{2R-{2β[2'R*,5'R*(S*)],5α(R*)}}-α-Decyloctahydro-α'-{[(1,1-dimethylethyl)diphenyl]silyloxymethyl}-2,2'-bifuran-5,5'-dimethanol-α-{[(1,1-dimethylethyl)dimethyl]silylether} (12)

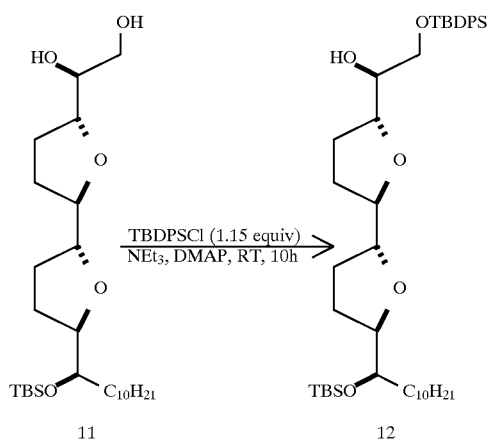

To a stirred suspension of 4 Å powdered molecular sieves in methylene chloride (16.5 mL) at −20° C. was added L-(+)-diethyl tartrate (0.26 mL, 60 mol %) followed by Ti(O$^i$Pr)$_4$ (0.39 mL, 50 mol %). After 10 min t-butyl hydroperoxide (1.39 mL, ~7.6 mmol, ~5.5M in octane) was added dropwise over a 5 min period. After stirred at −20° C. for 30 min, a solution of 10 (1.20 g, 2.55 mmol) in methylene chloride (8.5 mL) was added dropwise. The resulting solution was stirred at −20° C. for 4 h. Sodium hydroxide (10% aqueous solution, 0.8 mL) was added, and the solution was allowed to warm to room temperature. Ethyl acetate (30 mL) was added, and the solution was dried over anhydrous magnesium sulfate, filtered through Celite, and concentrated under reduced pressure to leave a light yellow oil. Flash chromatography (40% ethyl acetate in hexane, then 60% ethyl acetate in hexane) gave 0.46 g (38.3%) of the starting material 10 and 0.61 g (49.2%) of 11 as a colorless oil: $[\alpha]_D^{RT}$=+18.1° (c=1.82, CHCl$_3$); IR (neat) 3405, 1464, 1251, and 1066 cm$^{-1}$; $^1$H NMR (CDCl$_3$, 300 MHz) d 3.88–3.46 (m, 10 H, CH$_2$OH, CHOH, and CHO), 1.88–1.57 (m, 8 H, CHOH$_2$CH$_2$CHO), 1.40–1.30 (m, 2 H, CH$_2$CHOTBS), 1.19 (m, 16 H, CH$_2$), 0.79 [s, 9 H, C(CH$_3$)$_3$], 0.78 (t, J=6.3 Hz, CH$_2$CH$_3$), −0.00 (s, 3 H, SiCH$_3$), and −0.02 (s, 3 H, SiCH$_3$); $^{13}$C NMR (CDCl$_3$, 75.5 MHz) δ 82.01, 81.60, 81.43, 79.92, 74.43, 73.08, 63.79, 32.10, 31.59, 29.55, 29.29, 29.03, 28.19, 28.04, 26.99, 26.68, 25.65, 25.51, 22.35, 17.87, 13.78, −4.54, and −4.98. Anal. Calcd for C$_{27}$H$_{54}$O$_5$Si: C, 66.62%; H, 11.18%. Found: C, 66.73%; H, 11.12%.

To a stirred solution of 11 (0.76 g, 1.56 mmol) in methylene chloride (15 mL) was sequentially added triethylamine (0.91 mL, 6.50 mmol), 4-(N,N-dimethylamino) pyridine (44.6 mg, 20 mol %), and t-butyldiphenylsilylchloride (0.49 g, 1.80 mmol). After stirred at room temperature for 10 h, the mixture was quenched with brine (15 mL). The two layers were separated. The aqueous layer was extracted with ether (3×15 mL). The combined organic solutions were dried over anhydrous magnesium sulfate, filtered, and concentrated. Flash chromatography (10% ethyl acetate in hexane) of the residue gave 0. 98 g (86%) of 12 as a colorless oil: $[\alpha]_D^{RT}$=+11.8° (c=1.35, CHCl$_3$); IR (neat) 3455, 3071, 1472, 1428, and 1113 cm$^{-1}$; $^1$H NMR (CDCl$_3$, 300 MHz) δ 7.69 (m, 4 H, ArH), 7.40 (m, 6 H, ArH, 4.06–3.65 (m, 8 H, CH$_2$TBDPS and CHO), 2.52 (d, J=5 Hz, 1 H, OH, 2.00–1.68 (m, 8 H, CHOCH$_2$CH$_2$CHO), 1.45 (m, 2 H, CH$_2$CHOTBS), 1.28 (m, 16 H, CH$_2$), 1.08 [s, 9 H, SiPh$_2$C(CH$_3$)$_3$], 0.89 [m, 12 H Si(CH$_3$)$_2$C(CH$_3$)$_3$ and CH$_2$CH$_3$], and 0.59 (br s, 6 H, SiCH$_3$); $^{13}$C NMR (CDCl$_3$, 75.5 MHz) δ 135.46, 133.18, 133.09, 129.63, 127.64, 82.27, 81.89, 81.67, 78.50, 74.88, 73.00, 65.25, 32.21, 31.82, 29.78, 29.52, 29.25, 28.43, 28.27, 27.08, 26.98, 26.78, 25.89, 25.78, 22.60, 19.15, 18.12, 14.04, −4.30, and −4.76. Anal. Calcd for C$_{43}$H$_{72}$O$_5$Si$_2$: C, 71.22%; H, 10.01%. Found: C, 71.38%; H, 9.87%.

EXAMPLE 17

(+)-{2R-{2β[2'R*,5'R*(S*)],5α(R*)}}-α-
Decyloctahydro-α'-{[(1,1-dimethylethyl)diphenyl]
silyloxymethyl}-2,2'-bifuran-5,5'-dimethanol-α-}[(1,
1-dimethylethyl)dimethyl]silylether}-α'-(4-
methylbenzenesulfonate) (13)

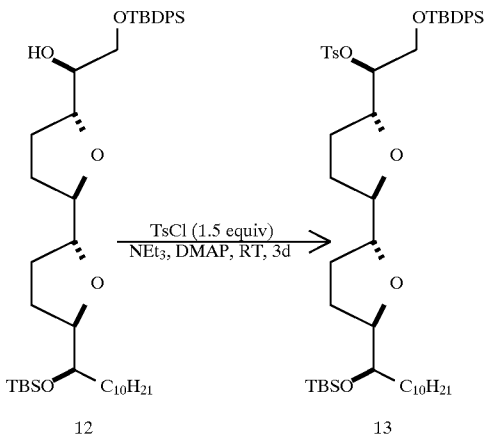

To a solution of 12 (0.98 g, 1.35 mmol) in methylene chloride (8 mL)were sequentially added triethylamine(0.75 mL, 5.40 mmol), 4-(N,N-dimethylamino)pyridine (33 mg, 20 mol %), and p-toluenesulfonyl chloride (0.52 g, 2.70 mmol). The resulting solution was stirred at room temperature for 3 days. Brine (10 mL) was added. The two layers were separated. The aqueous layer was extracted with ethyl acetate (3×10 mL). The combined organic solutions were dried over anhydrous magnesium sulfate, filtered and concentrated. Flash chromatography (10% ethyl acetate in hexane) of the residue gave 1.16 g (98%) of 13 as a colorless oil: $[\alpha]_D^{RT}$=+21.7° (c=1.07, CHCl$_3$); IR (neat) 3070, 1463, 1365, 1188, and 1112 cm$^{-1}$; $^1$H NMR (CDCl$_3$, 300 MHz) δ 7.77 (d, J=8.3 Hz, 2 H, ArH, 7.67 (m, 4 H, Ph-H), 7.44 (m, 6 H, Ph-H, 7.22 (d, J=8.3 Hz, ArH), 4.70 (ddd, J=4.5, 4.5, and 4.5 Hz, 1 H, CHOTs), 4.33 (ddd, J=4.5, 4.5, and 4.5 Hz, 1 H, CHOCHOTs), 3.93–3.62 (m, 6 H, CH$_2$OTBDPS, CHOCHO, and CHOCHOTBS), 2.39 (s, 3 H, ArCH$_3$), 2.04–1.30 m, 26 H, CH$_2$), 1.07 [s, 9 H, SiPh$_2$C(CH$_3$)$_3$], 0.92 [m, 12 H, Si(CH$_3$)$_2$C(CH$_3$)$_3$ and CH$_2$CH$_3$], 0.09 (s, 3 H, SiCH$_3$), and 0.08 (s, 3 H, SiCH$_3$); $^{13}$C NMR CDCl$_3$, 75.5 MHz) δ 144.27, 135.79, 135.74, 134.89, 133.23, 133.14, 129.90, 129.87, 129.76, 129.67, 128.01, 127.88, 83.83, 82.72, 81.79, 81.26, 77.38, 75.22, 63.24, 32.90, 32.09, 31.77, 30.06, 29.79, 29.52, 28.53, 28.29, 27.70, 27.43, 26.95, 26.18, 25.91, 22.86, 21.73, 19.38, 18.41, 14.30, –3.97, and –4.43. Anal. Calcd for C$_{50}$H$_{78}$O$_7$SSi$_2$: C, 68.29%; H, 8.94%. Found: C, 68.40%; H, 8.78%.

EXAMPLE 18

(+)-{2R-{2β[2'R*,5'R*(R*)],5α(R*)}}-α-
Decyloctahydro-5'-oxiranyl-2,2'-bifuran-5-methanol
(14)

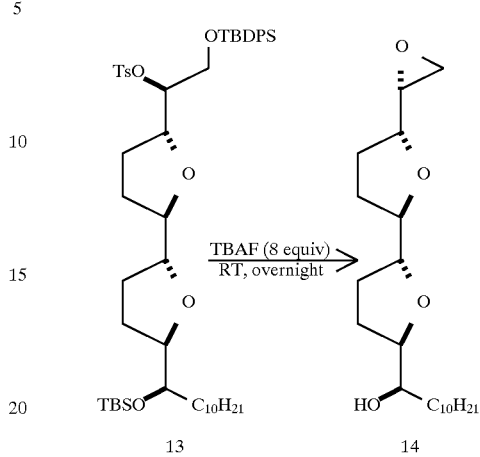

To a solution of 13 (1.16 g, 1.32 mmol) in tetrahydrofuran (5 mL) was added tetrabutylammonium fluoride (10.56 mL, 1M in THF). The resulting solution was stirred at room temperature overnight. The solvent was removed by evaporation under reduced pressure. Flash chromatography (80% ethyl acetate in hexane) of the thick, oil-like residue gave 0.41 g (88%) of 14 as a colorless oil: $[\alpha]_D^{RT}$=+7.0° (c=1.60, CHCl$_3$); IR (neat) 3469, 1464, 1194, and 1060 cm$^{-1}$; $^1$H NMR (CDCl$_3$, 300 MHz) δ 3.90–3.74 (m, 4 H, CHOCHOCH$_2$, CHOCHO, and CHOCHOH), 3.32 (m, 1 H, CHOH), 2.92 (ddd, J=4.1, 4.1, and 4.1 Hz, 1 H, CHOCH$_2$), 2.68 m, 2 H, CHOCH$_2$), 2.45 (br s, 1 H, OH), 1.96–1.20 (m, 26 H, CH$_2$), and 0.82 (t, J=6.3 Hz, 3 H, CH,); $^{13}$C NMR (CDCl$_3$, 75.5 MHz) δ 83.14, 82.40, 81.72, 78.85, 74.08, 54.25, 44.20, 33.53, 31.97, 29.81, 29.69, 29.41, 28.89, 28.86, 28.43, 25.73, 22.76, and 14.19. Anal. Calcd for C$_{21}$H$_{38}$O$_4$: C, 71.15%; H, 10.80%. Found: C, 70.94%; H, 10.60%.

EXAMPLE 19

(–)-{2R-{2,β[2'R*,5'R*(R*)],5α(R*)}}-α-
Decyloctahydro-α'-[3-(trimethylsilyl)-2-propynyl-2,
2'-bifuran-5,5'-dimethanol (3-a)

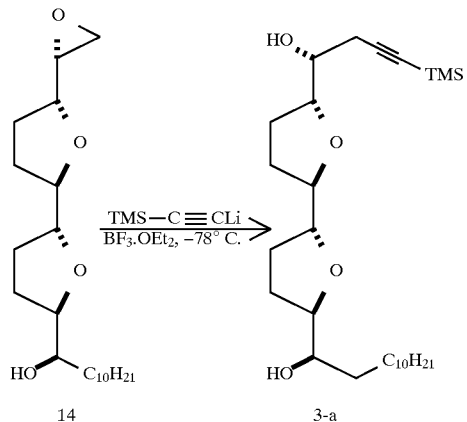

To a solution of trimethylsilylacetylene (0.11 mL, 0.78 mmol) in dry tetrahydrofuran (0.5 mL) was added n-butyllithium (0.32 mL, 2.5M in hexane, 2.8 equiv) at −78° C. The reaction mixture was stirred at −78° C. for 20 min. Boron trifluoride etherate (97 mL, 2.8 equiv) was added slowly. After the reaction mixture was stirred at −78° C. for 10 min., a solution of 14 (0.10 g, 0.28 mmol) in 0.4 mL of dry tetrahydrofuran was added. After 40 min at −78° C., the reaction was quenched with saturated ammonium chloride solution (10 mL). The mixture was extracted with ether (2×10 mL). The combined organic extracts were washed with 10 mL of water, dried over anhydrous magnesium sulfate, filtered, and concentrated. The residue was purified by flash chromatography (50% ethyl acetate in hexane) to give 94 mg (74%) of 3-a as a colorless oil: $[\alpha]_D^{RT}=-5.2'$ (c=0.55, CHCl$_3$); IR (neat) 3434, 2955, 2175, 1465, 1249, 1059, and 843 cm$^{-1}$; $^1$H NMR (CDCl$_3$, 300 MHz) δ 3.98 (ddd, J=6.4, 6.4, and 6.4 Hz, 1 H, CHIOCHOHCH$_2$C≡), 3.89–3.76 (m, 3 H, CHOCHO and CHOHCH$_2$CH$_2$), 3.55 (dddd, J=6.2, 6.2, 6.2, and 6.2 Hz, 1 H, CHOHCH$_2$C≡), 3.34 (m, 1 H, CHOHCH$_2$CH$_2$), 2.99 (br d, J=~5.3 Hz, CHOHCH$_2$C≡), 2.79 (br s, 1 H, CHOHCH$_2$CH$_2$), 2.45 (dd, J=6.2 and 17.9 Hz, 1 H, CH$_a$H$_b$C≡), 2.43 (dd, J=6.2 and 17.9 Hz, 1 H, CH$_a$H$_b$C≡), 1.99–1.92 (m, 5 H, from among CHOCH$_2$CH$_2$CHO), 1.82–1.61 (m, 3 H, from among CHOCH$_2$CH$_2$CHO), 1.36–1.32 (m, 2 H, CH$_2$CH$_2$CHOH), 1.25–1.19 (m, 16 H, CH$_2$), 0.86 (t, J=6.3 Hz, 3 H, CH$_2$CH$_3$), and 0.10 (s, 9 H, SiCH$_3$]; $^{13}$C NMR (CDCl$_3$, 75.5 MHz) δ 103.28, 86.49, 83.15, 82.10, 81.76, 81.51, 73.90, 71.00, 33.34, 31.38, 29.68, 29.54, 29.26, 29.90, 28.90, 28.28, 25.58, 25.34, 22.61, 14.04, and −0.00. Anal. Calcd for C$_{26}$H$_{48}$O$_4$Si: C, 68.98%; H, 10.69%. Found: C, 69.12%; H, 10.86%.

EXAMPLE 20

(−)-{2R-{2β[2'R*,5'R*(R*)],5α(R*)}}-α-Decyloctahydro-α'-(2-propynyl-2,2'-bifuran-5,5'-dimethanol (3)

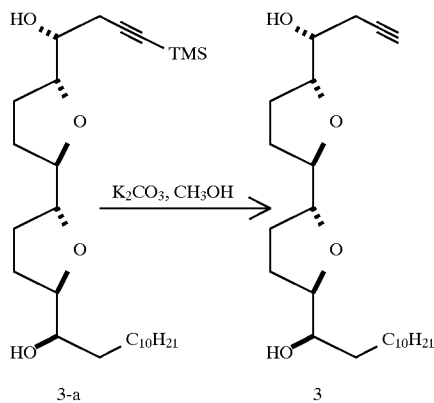

To a solution of 3-a (75 mg, 0.17 mmol) in methanol (1.0 mL) was added potassium carbonate (6.9 mg, 30 mol %) at room temperature. The resulting solution was stirred for 2 h, and was transferred into a fimnel containing 10 g of silica gel and eluted with 1:1 ethyl acetate in hexane. Concentration of the eluent gave 59 mg (94%) of 3 as a colorless oil: $[\alpha]_D^{RT}=-4.2°$ (c=0.57, CHCl$_3$); IR (neat) 3429, 3312, 2119, 1458, and 1098 cm$^{-1}$; $^1$H NMR (CDCl$_3$, 300 MHz) δ 3.99 (ddd, J=7.7, 5.8, and 5.8 Hz, 1 H, CHOCHOHCH$_2$C≡), 3.89–3.75 (m, 3 H, CHOCHO and CHOCHOHCH$_2$CH$_2$), 3.56 (m, 1 H, CHOHCH$_2$C≡), 3.33 (ddd, J=4.9, 4.9, and 4.9 Hz, CHOHCH$_2$CH$_2$), 3.21 (br s, 1 H, OH), 2.93 (br s, 1 H, OH, 2.41–2.35 (m, 2 H, CH$_2$C≡), 1.97–1.91 (m, 5 H, from among CHOCH$_2$CH$_2$CHO and C≡CH], 1.79–1.55 (m, 4 H, from among CHOCH$_2$CH$_2$CHO), 1.43–1.32 (m, 2 H, CH$_2$CH$_2$CHOH), 1.26–1.18 (m, 16 H, CH$_2$), and 0.88 (t, J=6.4 Hz, 3 H, CH$_2$CH$_3$); $^{13}$C NMR (CDCl$_3$, 75.5 MHz) δ 83,41, 82.44, 82.02, 81.60, 81.12, 74.15, 72.11, 70.31, 33.58, 32.10, 29.95, 29.81, 29.53, 29.17, 28.57, 28.49, 25.85, 24.05, 22.88, and 14.31. Anal. Calcd for C$_{23}$H$_{40}$O$_4$: C, 72.59%; H, 10.59%. Found: C, 72.43%; H, 10.68%.

EXAMPLE 21

(+)-{2R-{2β[2'R*,5'R*(R*)],5α(S*)}}-α-Decyloctahydro-5'-oxiranyl-2,2'-bifuran-5-methanol-α-(4-nitrobenzoate) (4-a)

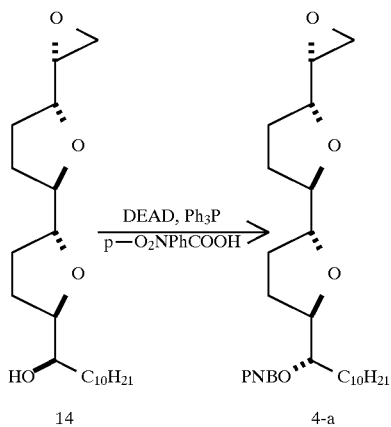

To a solution of 14 (150 mg, 0.42 mmol), triphenylphosphine (0.67 g, 2.54 mmol), and p-nitrobenzoic acid (0.42 g, 2.54 mmol) in benzene (1.0 mL), was added dropwise diethylazodicarboxylate (0.40 mL, 2.54 mmol). The resulting solution was stirred at room temperature for 10 h. After the solvent was removed by evaporation under reduced pressure, the solid-like residue was dissolved in a small amount of boiling ethyl acetate. Hexane was added until cloudy while the solution was still boiling. The mixture was cooled to ~−20° C., where some solid precipitated. The solid was removed by vacuum filtration. The filtrate was concentrated. Flash chromatography (40% ethyl acetate in hexane) of the residue gave 108 mg (51%) of 4-a as a light yellow wax: $[\alpha]_D^{RT}=+0.9°$ (c=1.39, CHCl$_3$); IR (neat) 3111, 3053, 1764, 1716, 1607, 1531, and 1270 cm$^{-1}$; $^1$H NMR (CDCl$_3$, 300 MHz) δ 8.24 (d, J=8.3 Hz, 2 H, ArH), 8.16 (d, J=8.3 Hz, 2 H, ArH), 5.17 (ddd, 6.7, 5.5, and 5.5 Hz, 1 H, CHOPNB), 4.10 (ddd, J=5.0, 5.0, and 5.0 Hz, 1 H, CHOCHOCH$_2$), 3.91–3.63 (m, 3 H, CHOCHO and CHOCHOPNB), 2.92 (ddd, J=4.0, 4.0, and 4.0 Hz, 1 H, CHOCH$_2$), 2.69–2.65 (m, 2 H, CHOCH, 2.06–1.91 (mn, 4 H, from among CHOCH$_2$CH$_2$CHO), 1.81–1.66 (m, 6 H, from among CHOCH$_2$CH$_2$CHO and CH$_2$CHOPNB), 1.25–1.18 (m, 16 H, CH$_2$), and 0.88 (t, J=6.4 Hz, 3 H, CH$_2$CH$_3$); $^{13}$C NMR (CDCl$_3$, 75.5 MHz) δ 164.00, 150.22, 135.75, 130.45, 123.27, 81.88, 81.67, 80.14, 78.68, 76.86, 53.93, 43.84, 31.61, 30.91, 29.27, 29.21, 29.03, 28.58, 27.96, 27.39, 25.19, 22.40, and 13.83. Anal. Calcd for C$_{28}$H$_{41}$NO$_7$: C, 66.78%; H, 8.21%. Found: C, 66.71%; H, 8.16%.

EXAMPLE 22

(-)-{2R-2β[2'R*,5'R*(R*)],5α(S*)}}-α-Decyloctahydro-α'-[3-(trimethylsilyl)-2-propynyl]-2,2'-bifuran-5,5'-dimethanol-α-(4-nitrobenzoate) (4-b)

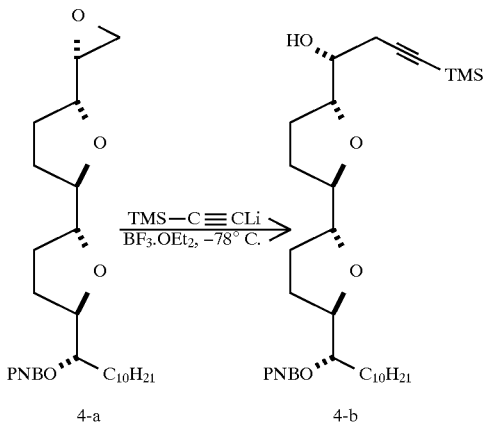

To a solution of trimethylsilylacetylene (57 mL, 0.40 mmol) in dry tetrahydrofuran (0.4 mL) was added n-butyllithium (95 mL, 2.5M in hexane, 1.2 equiv) at −78° C. The reaction mixture was stirred at −78° C. for 20 min. Boron trifluoride etherate (37 mL, 1.5 equiv) was added slowly. After the reaction mixture was stirred at −78° C. for 10 min, a solution of 4-a (0.10 g, 0.20 mmol) in 0.5 mrL of dry tetrahydrofuran was added. After 40 min at −78° C., the reaction was quenched with saturated ammonium chloride solution (10 mL). The mixture was extracted with ether (2×10 mL). The combined organic extracts were washed with 10 mL of water, dried over anhydrous magnesium sulfate, filtered, and concentrated. The residue was purified by flash chromatography (25% ethyl acetate in hexane) to give 88 mg (74%) of 4-b as a colorless oil: $[\alpha]_D^{RT}$=−7.33 (C=0.30, CHCl$_3$); IR (neat) 3458, 3112, 2175, 1725, 1608, 1529, and 1272 cm$^{-1}$; $^1$H NMR (CDCl$_3$, 300 MHz) δ 8.26 (d, J=8.7 Hz, 2 H ArH, 8.17 (d, J=8.7 Hz, 2 H ArH, 5.22 (ddd, J=5.2, 5.2, and 5.2 Hz, 1 H, CHOPNB), 4.13 (ddd, J=6.6, 6.6, and 6.6 Hz, 1 H, CHOCHOPNB or CHOCHOH ), 3.95 (ddd, J=6.6, 6.6, and 6.6 Hz, 1 H, CHOCHOH or CHOCHOPNB), 3.88–3.84 (m, 2 H, CHOCHO), 3.55 (ddd, J=5.8, 5.8, and 5.8 Hz, 1 H, CHOH), 2.58 (br s, 1 H, OH), 2.44 (dd, J=17.8 and 6.1 Hz, 1 H, CH$_a$H$_b$C∫), 2.42 (dd, J=17.8 and 6.1 Hz, 1 H, CH$_a$H$_b$C∫), 2.05–1.94 (m, 4 H, from among CHOCH$_2$CH$_2$CHO), 1.89–1.79 (m, 6 H, from among CHOCH$_2$CH$_2$CHO and CH$_2$CHOPNB), 1.27–1.12 (m, 16 H, CH$_2$), 0.86 (t, J=6.4 Hz, 3 H, CH$_2$CH$_3$), and 0.10 (s, 9 H, SiCH$_3$); $^{13}$C NMR (CDCl$_3$, 75.5 MHz) δ 164.22, 150.44, 135.90, 130.66, 123.49, 103.12, 86.67, 82.03, 81.84, 81.50, 80.47, 77.00, 72.01, 31.82, 31.18, 29.48, 29.39, 29.23, 28.69, 28.26, 27.58, 25.43, 25.34, 22.60, 14.04, and 0.01; HRMS (CI, NH$_3$ as ionizing gas) calcd for C$_{33}$H$_{55}$N$_2$O$_7$Si (M+NH$_4^+$): 619.3778. Found: 619.3753.

EXAMPLE 23

(-)-{2R-{2β[2'R*,5'R*(R*)],5α(S*)}}-α-Decyloctahydro-a'-[2-propynyl]-2,2'-bifuran-5,5'-dimethanol (4)

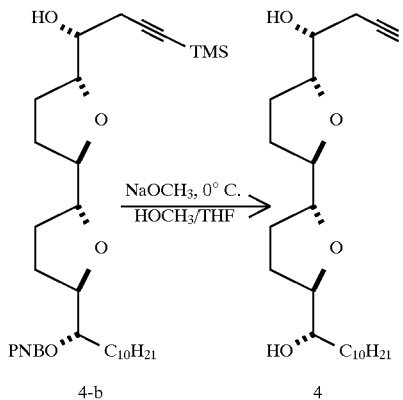

To a solution of 4-b (70 mg, 0.12 =mol) in methanol/tetrahydrofuran (0.5 mL, 1:1) was added sodium methoxide (1.2 mag, 20 mol %) at 0° C. The resulting solution was stirred at 0° C. for 4 h, and was transferred into a fiunel containing ~10 g of silica gel and eluted with 1:1 ethyl acetate in hexane. Concentration of the eluent gave 42 mg (94%) of 4 as a colorless oil: $[\alpha]_D^{RT}$=−6.2° (c=0.77, CHCl$_3$); IR (neat) 3429, 3312, 2119, 1458, and 1098 cm$^{-1}$; $^1$H NMR (CDCl$_3$, 500 MHz) δ 8 4.06 (ddd, J=8.5, 6.0, and 6.0 Hz, 1H, CH$_2$CH$_2$CHOHCHO or CHCHOHCH$_2$C≡), 3.93 (m, 3H, CHCHOHCH$_2$C≡ or CH$_2$CH$_2$CHOHCHO, CHOCHO), 3.88 (m, 1H, CH$_2$CH$_2$CHOH), 3.64 (dddd, J=5.5, 5.5, 5.5, and 5.5 Hz, 1H, 1H, ≡CCH$_2$CHOH), 3.21 (br d, J=~5.5 Hz, 1 H, OH), 2.79 (br d, J=~5.5 Hz, 1 H, OH), 2.45 (ddd, J=17.3, 5.5, and 3.0 Hz, 1H, CH$_a$H$_b$C≡C), 2.44 (ddd, J=17.3, 5.5, and 3.0 Hz, 1 H, CCH$_a$H$_b$C≡C), 2.06–1.96 (m, 4H, from among CHOCH$_2$CH$_2$CHO and C≡CH), 1.90 (m, 1H, from among CHOCH$_2$CH$_2$CHO), 1.84–1.73 (m, 2H, from among CHOCH$_2$CH$_2$CHO), 1.73–1.60 (m, 2H, from among CHOCH$_2$CH$_2$CHO), 1.50 (m, 1H, CH$_a$H$_b$C≡), 1.40–1.22 (m, 17H, CH$_a$H$_b$C≡ and CH$_2$), and 0.88 (t, 3H, J=7.3 Hz, CH$_2$CH$_3$); $^{13}$C NMR (CDCl$_3$, 75.5 MHz) δ 82.98, 82.76, 82.65, 81.89, 80.92, 72.29, 71.40, 70.17, 32.45, 32.02, 29.81, 29.74, 29.67, 29.45, 29.12, 28.57, 26.19, 24.52, 23.69, 22.79, and 14.23. Anal. Calcd for C$_{23}$H$_{40}$O$_4$: C, 72.59%; H, 10.59%. Found: C, 72.86%; H, 10.77%.

EXAMPLE 24

Oct-7-en-1-ol (15-a)

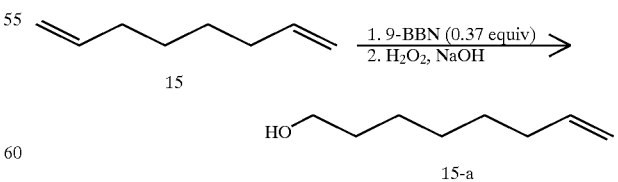

9-BBN (80 mL, 0.5M in THF, 40 mmol) was added slowly (in 3 h with a syringe pump) into 15 (16.0 mL, 108 mmol) with stirring at room temperature. The resulting solution was stirred for another 3 h. Ethanol (33 mL) was added, followed by sodium hydroxide solution (11 mL, 6N). Hydrogen peroxide (22 mL, 30%) was then added slowly (be very careful). The resulting solution was stirred at room temperature for 2 h. The aqueous layer was saturated with solid potassium carbonate. The two layers were separated. The aqueous layer was extracted with ether (50 mL). The combined organic solutions were dried over anhydrous magnesium sulfate, filtered, and concentrated. Flash chromatography (35% ethyl acetate in hexane) of the residue gave 3.86 g (75%) of 15-a as a colorless oil: IR (neat) 3338, 1641, 1462, 1057 and 909 cm$^{-1}$; $^1$H NMR (CDCl$_3$, 300 MHz) δ 5.67 (ddt, J=10.1, 18.0, and 6.7 Hz, 1 H, CH=CH$_2$), 4.87 (dd, J=18.0 and 1.3 Hz, 1 H, CH=CH$_a$H$_b$), 4.82 (dd, J=10.1 and 1.3 Hz, 1 H, CH=C$_a$H$_b$), 3.44 (t, J=6.8 Hz, 2 H, CH$_2$OH), 1.94 (dt, J=6.6 and 6.6 Hz, 2 H, CH$_2$CH=CH$_2$), 1.75–1.24 (m, 8 H, CH$_2$); $^{13}$C NMR (CDCl$_3$, 75.5 MHz) δ 138.58, 113.63, 62.01, 33.37, 32.24, 28.59, and 28.53.

EXAMPLE 25

(+)-(R)-1,2,8-Octanetriol (16)

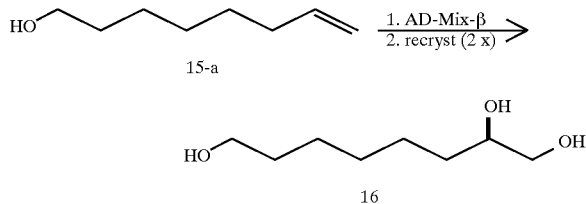

A 500-mL round-bottomed flask, equipped with a magnetic stirrer, was charged with 150 mL of t-butyl alcohol, 150 nL of water and 42.0 g of AD-mix-β. Stirring at room temperature produced two clear phases, the lower aqueous phase appears bright yellow. The mixture was cooled to 0° C. whereupon some of the dissolved salts precipitated. Compound 15-a (3.84 g, 30 mmol) was added at once, and the heterogeneous slurry was stirred vigorously at 0° C. for 6 h. While the mixture was stirred at 0° C., sodium sulfite was added. The reaction mixture was allowed to warm to room temperature and stirred for 1 h. After the separation of the two layers, the aqueous layer was further extracted with ethyl acetate (3×100 mL). The combined organic solutions were dried over anhydrous magnesium sulfate, filtered, and concentrated. Flash chromatography (10% methanol in ethyl acetate) gave 3.95 g (81%) of 16 as a white solid, which was ~80% ee by analyzing its Mosher ester derivative. Recrystallization from ethyl acetate (2×) gave 3.2 g (81% recovery) of the enantiomerically pure 16: mp 61°–62° C.; [α]$_D^{RT}$=+11.6°(c=1.03, CH$_3$OH); IR (KBr pellet) 3274, 1355, 1135, and 1049 cm$^{-1}$; $^1$H NMR (CDCl$_3$ and CD$_3$OD, 300 MHz) δ 4.54–4.31 (m, 3 H, OH), 3.14 (m, 5 H, CHOH and CH$_2$OH), 1.12–0.93 (m, 10 H, CH$_2$); $^{13}$C NMR (CDCl$_3$ and CD$_3$OD, 75.5 MHz) δ 71.71, 65.98, 61.64, 32.63, 31.93, 29.02, and 25.26. Anal. Calcd for C$_8$H$_{18}$O$_3$: C, 59.23%; H, 11.18%. Found: C, 59.14%; H, 11.24%.

EXAMPLE 26

(+)-(R)-6,6-Dimethoxyhexyloxirane (17)

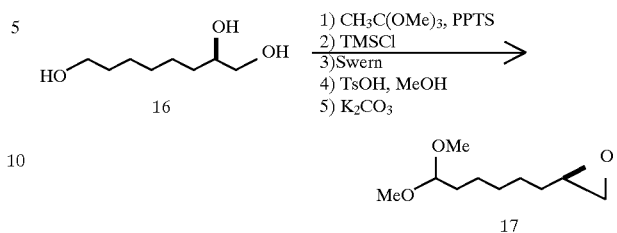

To a solution of 16 (3.0 g, 18.52 mmol) in methylene chloride (38 mL) was added trimethyl orthoacetate (2.5 mL, 19.45 mmol), followed by pyridinium p-toluenesulfonate (46.4 mg, 0.19 mnol). After stirred at room temperature for 20 min, trimethylsilyl chloride (3.13 ml, 24.67 mmol) was added. After 20 min, the solvent was removed by evaporation under reduced pressure. Methylene chloride (15 mL) was added. The solution was cooled to –78° C., whereupon a preprepared solution of anhydrous dimethyl sulfoxide and oxalic chloride (This solution was prepared by dissolving 38.7 mmol of DMSO in 7.7 mL of CH$_2$Cl$_2$, followed by the addition of 10.2 mL of 2M oxalic chloride methylene chloride solution at –60° C. to –70° C. The solution was kept at –60° C. to –70° C. for 0.5 h before use) was added via canal. The resulting solution was stirred at –70° C. for 2 h. Trimethylamine (11.8 mL, 84.40 mmol) was added. After the reaction mixture was warmed to room temperature, the solvent was removed by evaporation under reduced pressure. Methanol (38 mL) was added, followed by p-toluenesulfonic acid monohydrate (0.53 g, 15 mol %). After 2 h, potassium carbonate (6.36 g, 46.30 mmol) was added. The reaction mixture was stirred at room temperature for 10 h. Methanol was removed under reduced pressure. Water (50 mL) was added. The solution was extracted with ether (3×40 mL). The combined extracts were dried over anhydrous magnesium sulfate, filtered and concentrated. Flash chromatography (35% ethyl acetate in hexane) of the residue gave 3.0 g (86%) of 17 as a colorless oil: [α]$_D^{RT}$= +8.0° (c=2.21, CHCl$_3$); IR (neat) 2829, 1385, 1365, 1191, and 1128 cm$^{-1}$; $^1$H NMR (CDCl$_3$, 300 MHz) δ 4.32 (t, J=5.7 Hz, 1 H, CHOCH$_3$), 3.28 (s, 6 H, OCH$_3$), 2.86 (m, 1 H, CHOCH$_2$O), 2.70 (dd, J=5.0 and 4.0 Hz, CH$_a$H$_b$O), 2.42 (dd, J=5.1 and 2.7 Hz, CH$_a$H$_b$O), and 1.58–1.34 (m, 10 H, CH$_2$); $^{13}$C NMR (CDCl$_3$, 75.5 MHz) δ 104.70, 52.81, 52.44, 47.20, 32.59, 32.55, 26.07, and 24.13. Anal. Calcd for C$_{10}$H$_{20}$O$_3$: C, 63.80%; H, 10.71%. Found: C, 63.44%; H, 10.67%.

EXAMPLE 27

(+)-4-Trimethylsilylbut-3-yn-2-ol (ii-a)

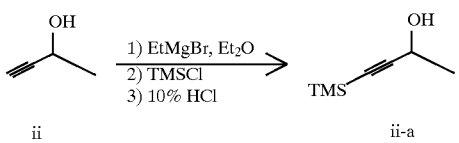

To a solution of ii (10.0 g, 0.14 mol) in ether (200 mL) was added ethylmagnesium bromide (105 mL, 3M in THF, 0.32 mol) dropwise at 0° C. The resulting solution was refluxed for 1.5 h. After the reaction solution was cooled to 0° C., trimethylsilyl chloride (40 mL, 0.32 mol) was added. The solution was warmed to room temperature and stirred overnight. Hydrochloric acid (100 mL, 10%) was added at 0° C. After 20 min, the two layers were separated. The aqueous layer was extracted with ether (2×50 mL). The combined organic solutions were dried over anhydrous magnesium sulfate, filtered and concentrated. Distillation of the residue gave 19.9 g (98%) ii-a as a colorless liquid: bp 80.5°–83.5° C./17.5 mm Hg; IR (neat) 3337, 2175, 1452, 1251, 1119, 1048, and 946 cm$^{-1}$; $^1$H NMR (CDCl$_3$, 300 MHz) δ 4.42 (q, J=6.6 Hz, 1 H, CHOH), 3.12 (br S, 1 H, OH), 1,16 (d, J=6.6 Hz, 3 H, CHCH$_3$), and 0.08 (s, 9 H, SiCH$_3$); $^{13}$C NMR (CDCl$_3$, 75.5 MHz) δ 108.12, 88.19, 58.61, 24. 05, and 0.01.

EXAMPLE 28

(–)-(S)-4-Trimethylsilylbut-3-yn-2-ol (ii-b)

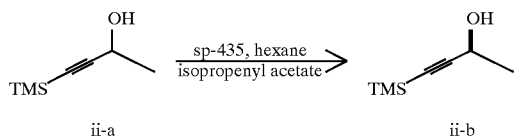

To a solution of ii-a (19.0 g, 0.13 mol) in hexane (400 mL) was added isopropenyl acetate (53.6 g, 0.54 mol) and SP-435 (Novo Nordisk, 1.9 g). The resulting solution was heated to 65° C. and stirred for 72 h. The enzyme was removed by filtration. The filtrate was concentrated by evaporation under reduced pressure. Medium pressure liquid chromatography of the residue (15% ether in pentane) gave 7.8 g (41%) of ii-b: [a]\|S(RT,D) =–25.6° (c=0.59, CHCl$_3$); The same set of spectra data as ii-a was obtained, and no diastereomer observed by MTPA analysis.

EXAMPLE 29

(–)-(S)-(1,1-Dimethylethyl)dimethyl[(1-methyl-2-propynyl)oxy]silane (18-a)

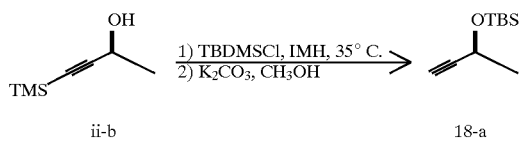

To a solution of ii-b (2.25 g, 15.9 mmol) in N,N-dimethyl formamide (2.5 mL) was added t-butyldimethylsilylchloride (2.81 g, 18.6 mmol), followed by imidazole (2.64 g, 38.8 mmol). The resulting solution was heated to 35° C. and stirred overnight. Water (20 mL) was added, and the solution was extracted with ether (3×30 mL). The combined extracts were dried over anhydrous magnesium sulfate, filtered, and concentrated. The residue was dissolved in 25 mL of methanol, potassium carbonate (0.60 g, 4.3 mmol) was added. After 1.5 h, the solution was transferred into a funnel containing ~50 g of silica gel and eluted with pentane (250 mL). Concentration of the eluent gave 2.62 g (90%) of 18-a as a colorless liquid: [α]$_D^{RT}$=–46.3° C. (c=1.36, CHCl$_3$); IR (neat) 3314, 2986, 1472, 1255, 1122, 1059, and 838 cm$^{-1}$ $^1$H NMR (CDCl$_3$, 300 MHz) 8 4.47 (dq, J=2.0 and 6.5 Hz, 1 H, CHO), 2.32 (d, J=2.0 Hz, 1 H, HC≡C), 1.38 (d, J=6.5 Hz, 3 H, OCHCH$_3$), 0.88 [s, 9 H, SiC(CH$_3$)$_3$], 0.11 (s, 3 H, SiCH$_3$), 0.09 (s, 3 H, SiCH$_3$); $^{13}$C NMR (CDCl$_3$, 75.5 MHz) δ 86.13, 70.99, 58.54, 25.53, 25.09, 17.93, –4.88, and –5.27.

EXAMPLE 30

(–)-[2S,(2R*,6S*)]-12,12-Dimethoxy-2-[(1,1-dimethylethyl)dimethyl]silyoxydodec-3-yn-6-ol (19)

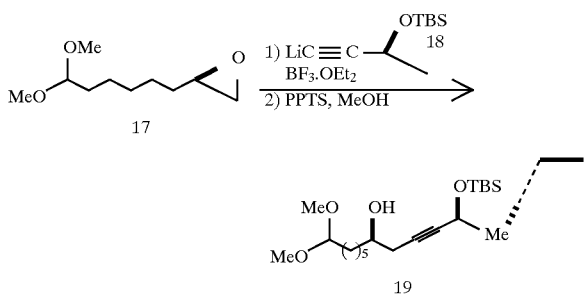

To a solution of 18-a (1.42 g, 7.71 mmol) in dry tetrahydrofuran (12 mL) was added n-butyllithium (3.1 mL, 2.5M in hexane, 7.71 mmol) at –78° C. The reaction mixture was stirred at –78° C. for 20 min. Boron trifluoride etherate (0.82 mL, 6.7 mmol) was added slowly. After the reaction mixture was stirred at –78° C. for 10 min, a solution of 17 (1.26 g, 6.70 mmol) in 3 mL of dry tetrahydrofuran was added. After 40 min at –78° C., the reaction was quenched with water (50 mL). The mixture was extracted with ether (4×50 mL). The combined organic extracts were washed with 50 mL of water, dried over anhydrous magnesium sulfate, filtered, and concentrated. The residue (containing ~15% of aldehyde) was dissolved in 8 mL of methanol, and 50 mg (~5 mol %) of pyridinium p-toluenesulfonate and 0.81 mL of trimethyl orthoacetate were added. The solution was stirred at room temperature for 1 h and transferred into a funnel containing ~50 g of silica gel and eluted with 1:1 ethyl acetate/hexane (220 mL). The eluent was concentrated, and the residue was purified by flash chromatography (40% ethyl acetate in hexane) to give 2.17 g (88%) of 19 as a colorless oil: MTPA analysis indicated the shown configuration at C(6); [a]$_D^{RT}$= –37.0° (C=3.09, CHCl$_3$); IR (neat) 3458, 1414, 1253, 1159, and 834 cm$^{-1}$; $^1$H NMR (CDCl$_3$, 300 MHz) δ 4.44 (q, J=6.4 Hz, 1 H, CHCH$_3$), 4.28 (t, J=5.7 Hz, 1 H, CHOCH$_3$), 3.62 (m, 1 H, CHOH), 3.23 (s, 6 H, OCH$_3$), 2.37–2.17 (m, 3 H, C≡CCH$_2$CHOH), 1.51–1.27 (m, 13 H, CH$_2$ and CHCH$_3$), 0.83 [s, 9 H, SiC(CH$_3$)$_3$], 0.04 (s, 3 H, SiCH$_3$), and 0.03 (s, 3 H, SiCH$_3$). $^{13}$C NMR (CDCl$_3$, 75.5 MHz) δ 104.29, 85.20, 79.58, 69.73, 58.95, 52.35, 35.93, 32.21, 29.22, 27.50, 25.62, 25.50, 25.35, 24.36, 18.05, –4.80, and –5.11. Anal. Calcd for C$_{20}$H$_{40}$O$_4$Si: C, 64.47%; H, 10.82%. Found: C, 64.31%; H, 10.75%.

EXAMPLE 31

(–)-[2S,(2R*, 6S*)]-12,12-Dimethoxy-2-[(1,1-dimethylethyl)dimethyl]silyloxy-6-[(1,1-dimethylethyl)diphenyl]silyloxvdodec-3-yne (20)

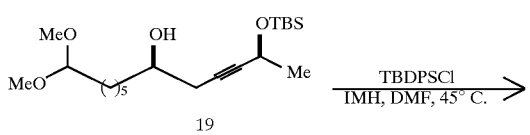

-continued

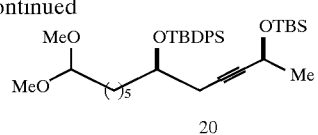

Into a 25-mL round-bottomed flask were sequentially added 19 (1.32 g, 3.55 mmol), t-butyldiphenylsilylchloride (1.17 g, 1.20 equiv), imidazole (0.60 g, 2.50 equiv), and N,N-dimethyl formamide (6.0 mL). The reaction mixture was stirred in an argon atmosphere at 45° C. for 4 h. After the reaction mixture was cooled to room temperature, ether (20 mL) was added. The solution was washed with water (2×15 mL), dried over anhydrous magnesium sulfate, filtered, and concentrated. The residue was purified by flash chromatography (5% ethyl acetate in hexane) to give 2.02 g (93%) of 20 as a colorless oil: $[\alpha]_D^{RT}=-13.4°$ (C=1.20, CHCl$_3$); IR (neat) 3071, 3050, 1471, 1428, and 702 cm$^{-1}$; $^1$H NMR (CDCl$_3$, 300 MHz) δ 7.69 (m, 4 H, ArH), 7.41 (m, 6 H, ArH), 4.48 (q, J=6.3 Hz, 1 H, CHCH$_3$), 4.34 (t, J=5.7 Hz, 1 H, CHOCH$_3$), 3.83 (dddd, J=5.6, 5.6, 5.6, and 5.6 Hz, 1 H, CHOTBDPS), 3.31 (s, 6 H, OCH$_3$), 2.34–2.29 (m, 2 H, C≡CCH$_2$), 1.56–1.52 (m, 4 H, CH$_2$CHOCH$_3$ and CH$_2$CH$_2$CHOTBDPS), 1.35 (d, J=6.3 Hz, 3 H, CHCH$_3$), 1.28–1.10 (m, 6 H, CH$_2$), 1.07 [s, 9 H, SiPh$_2$C(CH$_3$)$_3$], 0.90 [s, 9 H, Si (CH$_3$)$_2$C(CH$_3$)$_3$], and 0.10 [s, 6 H, Si (CH$_3$)$_2$C(CH$_3$)$_3$]; $^{13}$C NMR (CDCl$_3$, 75.5 MHz) δ 135.93, 134.37, 134.14, 129.64, 129.61, 127.60, 127.54, 104.55, 84.48, 80.39, 71.65, 59.25, 52.56, 35.97, 32.47, 29.53, 27.06, 26.68, 25.90, 25.70, 24.68, 24.62, 19.39, 18.31, −4.50, and −4.86. Anal. Calcd for C$_{36}$H$_{58}$O$_4$Si$_2$: C, 70.77%; H, 9.57%. Found: C, 70.57%; H, 9.63%.

EXAMPLE 32

(+)-[2S,(2R*,6S*)]-12,12-Dimethoxy-6-[(1,1-dimethylethyl)diphenyl]silyloxydodec-3-yn-2-ol (21)

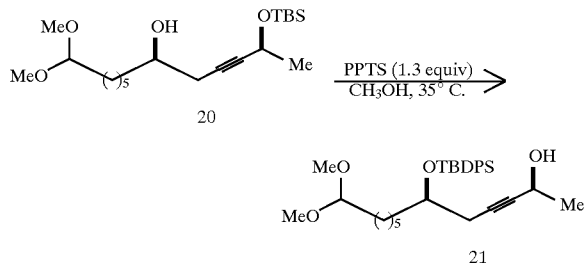

To a solution of 20 (1.30 g, 2.13 mmol) in 10 mL of methanol, pyridinium p-toluenesulfonate (0.70 g, 1.3 equiv) was added. The reaction mixture was stirred at 35° C. until TLC showed that all 20 was reacted (about 3.5 h). Methanol was removed under reduced pressure. To the residue, water (10 mL) and ether (20 mL) were added. The two layers were separated. The ether layer was washed with water (2×10 mL), dried over anhydrous magnesium sulfate, filtered, and concentrated. The residue was purified by flash chromatography (30% ethyl acetate in hexane) to give 0.91 g (86%) of 21 as a colorless oil: MTPA analysis indicated the shown configuration at C(2); $[\alpha]_D^{RT}=+1.83°$ (C=0.85, CHCl$_3$); IR (neat) 3443, 3071, 3049, 2246, 1428, and 704 cm$^{-1}$; $^1$H NMR (CDCl$_3$, 300 MHz) δ 7.69–7.67 (m, 4 H, ArH), 7.43–7.33 (m, 6 H, ArH), 4.40 (m, 1 H, CHOH), 4.32 (t, J=5.7 Hz, 1 H, CHOCH$_3$), 3.83 (dddd, J=5.6, 5.6, 5.6, and 5.6 Hz, 1 H, CHOTBDPS), 3.29 (s, 6 H, OCH$_3$), 2.33–2.28 (m, 2 H, C≡CCH$_2$), 1.56–1.50 (m, 4 H, CH$_2$CHOCH$_3$ and CH$_2$CH$_2$CHOTBDPS), 1.34 (d, J=6.3 Hz, 3 H, CHCH$_3$), 1.31–1.10 (m, 6 H, CH$_2$), and 1.05 [s, 9 H, SiPh$_2$C(CH$_3$)$_3$]; $^{13}$NMR (CDCl$_3$, 75.5 MHz) δ 135.76, 134.24, 133.63, 129.51, 129.45, 127.43, 127.34, 104.36, 83.93, 81.21, 71.48, 58.16, 52.39, 35.81, 32.14, 29.08, 26.87, 26.66, 24.39, 24.19, and 19.23. Anal. Calcd for C$_{30}$H$_{44}$O$_4$Si: C, 72.54%; H, 8.93%. Found: C, 72.78%; H, 8.72%.

EXAMPLE 33

(−)-[2S,(2R*,6S*),3Z]-4-Iodo-12,12-dimethoxy-6-[(1,1-dimethylethyl)diphenyl]silyloxydodec-3-en-2-ol (21-a)

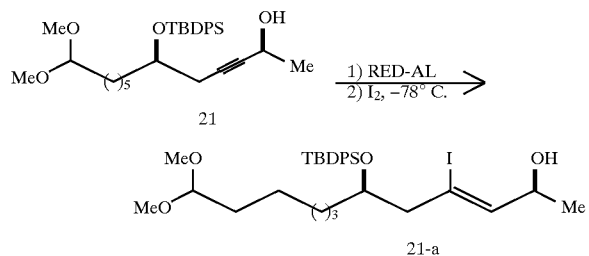

To a solution of 21 (0.63 g, 1.27 mmol) in 10.0 mL of dry tetrahydrofuran, sodium bis (2-methoxyethoxy) aluminum hydride (3.4M in toluene, 0.64 mL, 2.18 mmol) was added at 0° C. The reaction mixture was allowed to warm to room temperature, stirred for 5 h, and then was cooled to 0° C. again. Ethyl acetate (0.15 mL) was added. After stirred at 0° C. for 20 min, the solution was cooled to −78° C. A solution of iodine (0.55 g, 2.16 mmol) in 3.0 mL of tetrahydrofuran was added dropwise. The reaction mixture was stirred for another 30 min at −78° C., and then the cooling bath was removed. After 7 min, saturated sodium thiosulfate (8 mL) was added. After the mixture became colorless, the two layers were separated. The water layer was extracted with ether (3×10 mL). The combined organic solutions were washed with saturated sodium bicarbonate (20 mL), and water (20 mL), dried over anhydrous magnesium sulfate, filtered, and concentrated. Flash chromatography (30% ethyl acetate in hexane) of the residue gave 0.71 g (89%) of 21-a as a colorless oil: $[\alpha]_D^{RT}=-18.3°$ (C=1.53, CHCl$_3$); IR (neat) 3454, 3070, 3048, 1461, 1428, and 1111 cm$^{-1}$; $^1$H NMR (CDCl$_3$, 300 MHz) δ 7.71–7.69 (m, 4 H, ArH ), 7.44–7.35 (m, 6 H, ArH), 5.59 (d, J=7.3 Hz, 1 H, C=CH), 4.35–4.30 (m, 2 H, CHOCH$_3$ and CHOH), 4.05 (m, 1 H, CHOTBDPS), 3.29 (s, 6 H, OCH$_3$), 2.64 (dd, J=5.9 and 14.0 Hz, 1 H, C≡CCH$_a$H$_b$), 2.60 (dd, J=7.0 and 14.0 Hz, 1 H, C≡CCH$_a$H$_b$), 2.31 (bs, 1 H, OH), 1.51 (dt, J=7.6 and 5.9 Hz, 2 H, CH$_2$CH$_2$CHOTBDPS), 1.43–1.13 (m, 11 H, CH$_2$ and CHCH$_3$), and 1.07 [s, 9 H, SiPh$_2$C(CH$_3$)$_3$]; $^{13}$C NMR (CDCl$_3$, 75.5 MHz) δ 140.72, 135.95, 134.15, 134.03, 129.61, 127.57, 127.54, 104.38, 103.46, 72.50, 71.85, 52.48, 51.73, 35.22, 32.30, 29.26, 27.06, 24.42, 24.18, 21.78, and 19.38. Anal. Calcd for C$_{30}$H$_{45}$IO$_4$Si: C, 57.68%; H, 7.26%. Found: C, 57.58%; H, 7.10%.

EXAMPLE 34

(−)-{5S,[5R*,3(S*)]}-{8,8-Dimethoxy-2-[(1,1-dimethylethy)diphenyl]silyloxyoctyl}-5-methylfuran-2(5H)-one (22)

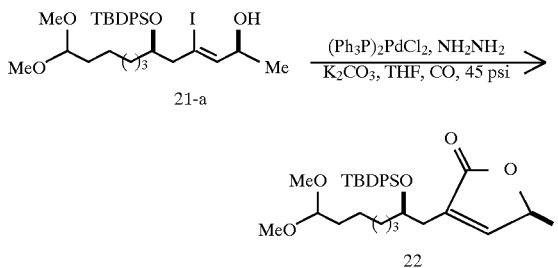

To a mixture of bis(triphenylphosphine)palladium (II) chloride (6.8 mg, 1 mol %) and anhydrous potassium carbonate (0.14 g, 0.96 mmol) in a carbonylation bomb, was added a solution of 21-a (0.60 g, 0.96 mmol) in 5 mL of dry tetrahydrofiaran followed by 1 drop of hydrazine. The mixture was stirred under an carbon monoxide atmosphere (45 psi) for 2 d at 35° C. Diethyl ether (30 mL) was then added and the mixture was filtered. After the solvent was removed, the residue was purified by flash chromatography (30% ethyl acetate in hexane) to give 0.47 g (93%) of 22 as a colorless oil: $[\alpha]_D^{RT}$=−9.3° (C=2.98, CHCl$_3$); IR (neat) 3071, 3049, 1756, 1428, and 1112cm$^{-1}$; $^1$H NMR(CDCl$_3$, 300MHz) δ 7.57 (t, J=6.7 Hz, 4 H, ArH), 7.28 (m, 6 H, ArH), 6.83 br s, 1 H, C=CH), 4.77 (q, J=6.5 Hz, 1 H, OCHCH$_3$), 4.20 (t, J=5.7 Hz, 1 H, CHOCH$_3$), 3.96 (dddd, J=5.7, 5.7, 5.7, and 5.7 Hz, 1 H, CHOTBDPS), 3.18 (s, 6 H, OCH$_3$), 2.36 (m, 2 H, CH$_2$C=), 1.44–1.30 (m, 4 H, CH$_2$CHOCH$_3$ and CH$_2$CH$_2$CHOTBDPS), 1.20 (d, J=6.8 Hz, 3 H, CHCH$_3$), 1.17–1.00 (m, 6 H, CH$_2$), 0.95 [s, 9 H, SiPh$_2$C (CH$_3$)$_3$]; $^{13}$C NMR (CDCl$_3$, 75.5 MHz) δ 173.95, 151.42, 135.91, 134.15, 134.09, 130.63, 129.77, 127.67, 104.55, 77.46, 71.77, 52.66, 36.37, 32.43, 31.97, 29.34, 27.11, 24.83, 24.48, 19.42, and 18.97. Anal. Calcd for C$_{31}$H$_{44}$O$_5$Si: C, 70.95%; H, 8.45%. Found: C, 71.19%; H, 8.22%.

EXAMPLE 35

(−)-{5S,[5R*,3(S*)]}-3-{2-[(1,1-Dimethylethyl)diphenyl]silyloxy-8-oxooctyl}-5-methylfuran-2(5H-one (22-a)

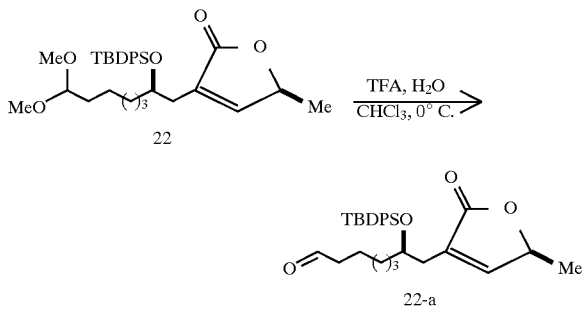

To a solution of 22 (0.35 g, 0.67 mmol) in chloroform (4 mL) at 0° C. was added a solution of trifluoroacetic acid (2 mL, 50% solution in water). After the resulting solution was stirred at 0° C. for 1.5 h, saturated sodium bicarbonate was added dropwise until no more carbon dioxide evolved. Ether (40 mL) was added, and the two layers were separated. The organic phase was washed with saturated sodium bicarbonate (10 mL) and water (10 mL) sequentially, dried over anhydrous magnesium sulfate, filtered, and concentrated. Flash chromatography (36% ethyl acetate in hexane) of the residue gave 0.30 g (94%) of 22-a as a colorless oil: $[\alpha]_D^{RT}$=−8.9° (C=0.55, CHCl$_3$); IR (neat) 3071, 3048, 3014, 2716, 1732, 1427, and 1028 cm$^{-1}$; $^1$H NMR (CDCl$_3$, 300 MHz) δ 9.66 (br s, 1 H, HC=O), 7.60 (t, J=7.2 Hz, 4 H, ArH), 7.30 (m, 6 H, ArH), 6.87 (br s, 1 H, C=CH), 4.81 (q, J=6.5 Hz, 1 H, OCHCH$_3$), 3.99 (dddd, J=5.7, 5.7, 5.7, and 5.7 Hz, 1 H, CHOTBDPS), 2.36 (m, 2 H, CH$_2$C=), 2.21 [t, J=7.2 Hz, 2 H, HC(O)CH$_2$], 1.44–1.32 (m, 4 H, CH$_2$CH$_2$CHO and CH$_2$CH$_2$CHOTBDPS), 1.22 (d, J=6.8 Hz, 3 H, CHCH$_3$), 1.20–1.02 (m, 4 H, CH$_2$), 0.98 [s, 9 H, SiPh$_2$C(CH$_3$)$_3$]; $^{13}$C NMR (CDCl$_3$, 75.5 MHz) δ 202.79, 174.16, 151.81, 136.07, 134.28, 134.19, 130.66, 129.97, 127.86, 77.69, 71.83, 43.88, 36.30, 32.13, 29.07, 25 27.28, 24.74, 22.02, 19.59, and 19.14. Anal. Calcd for C$_{29}$H$_{38}$O$_4$Si: C, 72.76%; H, 7.86%. Found: C, 72.60%; H, 7.86%.

EXAMPLE 36

(−)-{1S,[5R*,3(S*,E)]}- and (−)-5S,[5R*,3(S*,Z)]}-3-{9-Iodo-2-[(1,1-dimethylethyl)diphenyl]silyloxynon-8-enyl}-5-methylfuran-2(5H)-one (5)

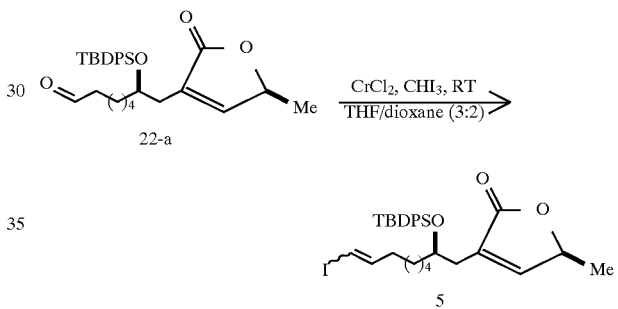

To a suspension of chromium chloride (0.49 g, 3.77 mmol) in tetrahydrofairan (3 mL) was added a solution of 22-a (0.28 g, 0.59 mmol) and iodoform (0.49 g, 1.26 mmol) in 1,4-dioxane (2 mL). After the resulting mixture was stirred at room temperature for 9.5 h, water (30 mL) was added. The mixture was extracted with ether (5×20 mL). The combined extracts were washed with saturated ammonium chloride (30 mL) and water (30 mL) sequentially, and then dried over anhydrous magnesium sulfate, filtered, and concentrated. Flash chromatography (15% ethyl acetate in hexane) gave 0.27 g (77%) of 5 as a light yellow oil with a E:Z ratio of approximately 4:1: $[\alpha]_D^{RT}$=−12.3° (C=0.83, CHCl$_3$); IR (neat) 3069, 3048, 3013, 1751, 1652, 1589, 1427, and 1109 cm$^{-1}$; $^1$H NMR (CDCl$_3$, 300 MHz, major isomer) δ 7.67 (t, J=7.2 Hz, 4 H, ArH), 7.38 (m, 6 H, ArH), 6.95(br s, 1 H, C=CH), 6.45 (dt J=14.3 and 7.1 Hz, 1 H, CH$_2$CH=), 5.92 (d, J=14.2 Hz, 1H, IHC=), 4.92 (q, J=6.5 Hz, 1 H, OCHCH$_3$), 4.02 (dddd, J=5.7, 5.7, 5.7, and 5.7 Hz, 1 H, CHOTBDPS), 2.45 (m, 2 H, CH$_2$C=), 1.96 [ddd, J=7.2, 7.2, and 7.2 Hz, 2 H, =CHCH$_2$], 1.44–1.37 (m, 2 H, CH$_2$CH$_2$CHOTBDPS), 1.32 (d, J=6.6 Hz, 3 H, CHCH$_3$), 1.28–1.08 (m, 6 H, CH$_2$) and 0.99 [s, 9 H, SiPh$_2$C(CH$_3$)$_3$]; $^{13}$C NMR (CDCl$_3$, 75.5 MHz, major isomer) δ 173.91, 151.33, 146.53, 135.80, 134.06, 133. 93, 130.52, 129.67, 127.56, 77.38, 74.37, 71.60, 36.11, 35.76, 31.75, 28.00, 24.47, 19.32, and 18.89; HRMS (EI) calcd for C$_{30}$H$_{39}$IO$_3$Si (M$^+$): 602.1715. Found: 602.1710.

EXAMPLE 37

(-)-2R-[2α[2'R*,5'R*)],5β[1(S*),2R*,8E,13R*]]]-3-[13-[5'-[1-(Hydroxy)undecyl]octahydro[2.2'-bifuran]-5-yl]-13-hydroxy-2-(dimethylethyl-diphenylsilyl)oxy-8-tridecen-10-ynyl]dihydro-5-methyl-2(5H)-furanone (23) and (-)-[2R-[2α[2'R*,5'R*(S*)],5β[1(S*),2R*,8E,13R*]]]-3-[13-[5'-[1-(Hydroxy)undecyl]octahydro[2.2'-bifuran]-5-yl]-13-hydroxy-2-(dimethylethyl-diphenylsilyl)oxy-8-tridecen-10-ynyl]dihydro-5-methyl-2(5H)-furanone (24)

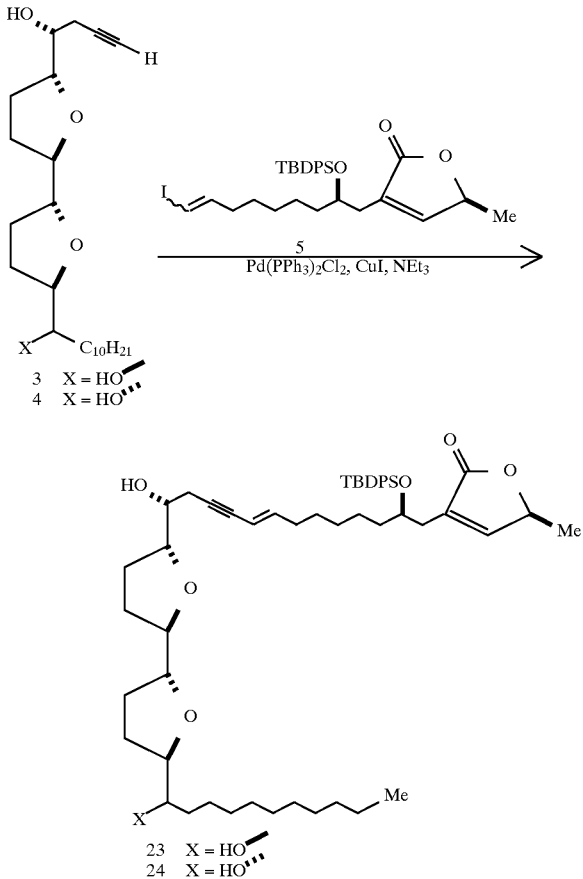

(a) To a stirred solution of 3 (40 mg, 0.11 mmol) in triethylame (1.0 mL) at RT was added 5 (95 mg, 0.16 mmol, 1.5 equiv), cuprous iodide (6.0 mg, 0.032 mol, 0.3 equiv), and bis(triphenylphosphine)palladium(II) chloride (7.4 mg, 10 mol %). After 10 h at RT the reaction mixture was diluted with water (5 mL) and ether (5 mL), the organic layer was separated, and the aqueous layer was extracted with ethyl acetate (3×5 mL). The organic layers were combined, washed with brine (5 mL), dried (MgSO$_4$), and concentrated under reduced pressure to leave a crude yellow oil. Flash chromatography (60% ethyl acetate in hexane) gave 71 mg (79%) of the enyne 23 as a yellow oil: $[\alpha]_D^{RT}$=-15.53 (c=0.92, CHCl$_3$); IR (neat) 3453, 3070, 3048, 3015, 1755, 1462, 1427, and 1065 cm$^{-1}$; $^1$H NMR (300 MHz, CDCl$_3$) δ 7.65 (t, J=7 Hz, 4 H, ArH), 7.39 (m, 6 H, ArH), 6.92 (br s, 1 H, HC=CC=O), 6.00 (dt, J=15.7 and 7.0 Hz, 1 H, =CHCH$_2$), 5.39 (br d, J=15.8 Hz, 1 H, C$f$CCHH=), 4.89 (q, J=6.7 Hz, 1 H, OCHH$_3$), 4.00 [m, 2 H, C(4, 16)H], 3.85 [m, 3 H, C(19, 20, 23)H], 3.59 [dddd, J=5.4, 5.4, 5.4, and 5.4 Hz, 1 H, C(15)H], 3.38 [m, 1 H, C(24)H], 2.93 (br s, 1 H, OH), 2.73 (br s, 1 H, OH), 2.53 [br d, J=5.2 Hz, 2 H, C(14)H$_2$], 2.44 [br d, J=4.9 Hz, 2 H, C(3)H$_2$], 1.97–1.92 [m, 4 H, from among C(17, 18, 21, 22)H$_2$], 1.78–1.62 [m, 4 H, from among C(17, 18, 21, 22)H$_2$], 1.36–1.18 [m, 28 H, C(5–9, 25–33)H$_2$], 1.03 [s, 9 H, SiPh$_2$C(CH$_3$)$_3$], and 0.87 (t, J=6.3 Hz, 3 H, CH$_2$CH$_3$); $^{13}$C NMR (CDCl$_3$, 75.5 MHz) δ 174.14, 151.49, 144.01, 136.01, 134.24, 134.18, 130.74, 129.88, 127.76, 109.81, 84.66, 83.38, 82.36, 81.99, 81.69, 81.18, 77.61, 74.18, 72.46, 71.83, 36.40, 33.60, 32.95, 32.08, 31.98, 29.92, 29.80, 29.50, 29.13, 29.00, 28.70, 28.53, 27.19, 25.83, 25.07, 24.80, 22.85, 19.52, 19.08, and 14.30.

(b) Enyne 24 was prepared the same way as 23 from the reaction of 4 (25 mg, 65.8 mmol) and 5 (98.7 mg, 1.5 equiv). Flash chromatography (60% ethyl acetate in hexane) gave 46 mg (82%) of the enyne 24 as a yellow oil: $[\alpha]_D^{RT}$=-28.3 (c=1.00, CHCl$_3$); IR (neat) 3439, 3070, 3047, 3015, 1751, 1427, and 1105 cm$^{-1}$; $^1$H NMR (500 MHz, CDCl$_3$) δ 7.65 (t, J=6.6 Hz, 4 H, ArH), 7.37 (m, 6 H, ArH), 6.92 (br s, 1 H, HC=CC=O), 6.00 (dt, J=15.7 and 7.0 Hz, 1 H, =CHCH$_2$), 5.39 (br d, J=15.8 Hz, 1 H, C$f$CCH=), 4.89 (q, J=6.7 Hz, 1 H, OCHH$_3$), 4.03–3.84 [m, 6 H, C(4, 16, 19, 20, 23, 24)H], 3.61 [m, 1 H, C(15)H], 3.16 (br s, 1 H, OH), 2.76 (br s, 1 H, OH), 2.50 [br d, J=5.5 Hz, 2 H, C(14)$_2$], 2.44 [br d, J=5.2 Hz, 2 H, C(3)H$_2$], 2.04–1.95 [m, 6 H, from among C(9, 17, 18, 21, 22)H$_2$], 1.81–1.53 [m, 4 H, from among C(5, 9, 17, 18, 21, 22, 25)H$_2$], 1.37–1.25 [m, 26 H, from among C(5–9, 25–33)H$_2$], 1.04 [s, 9 H, SiPh$_2$C(CH$_3$)$_3$], and 0.87 (t, J=6.3 Hz, 3 H, CH$_2$CH$_3$); $^{13}$C NMR (CDCl$_3$, 75.5 MHz) δ 174.01, 151.34, 143.86, 135.86, 134.11, 134.04, 130.61, 129.73, 127.62, 109.66, 84.50, 82.87, 82.84, 82.64, 81.83, 81.00, 77.47, 72.49, 71.69, 71.35, 36.25, 32.82, 32.42, 31.93, 31.82, 29.73, 29.65, 29.59, 29.36, 29.00, 28.87, 28.57, 28.45, 27.05, 26.10, 24.66, 24.49, 22.71, 19.38, 18.94, and 14.15.

EXAMPLE 38

(-)-[2R-[2α2'R*,5'R*(R*)],5β[1(S*),2R*,13R*]]]-3-[13-[5'-[1-(Hydroxy)undecyl]octahydro[2.2'-bifuran]-5-yl]-13-hydroxy-2-(dimethylethyl-diphenylsilyl)oxytridecyl]dihydro-5-methyl-2(5H)-furanone (1-a) and (-)α[2R-[2a[2'R*,5'R*(S*)],5β[1(S*),2R*,13R*]]]-3-[13-[5'-[1-(Hydroxy)undecyl]octahydro[2.2'-bifuran]-5-yl-13-hydroxy-2-(dimethylethyl-diphenylsilyl)oxytridecyl]dihydro-5-methyl-2(5H)-furanone (2-a)

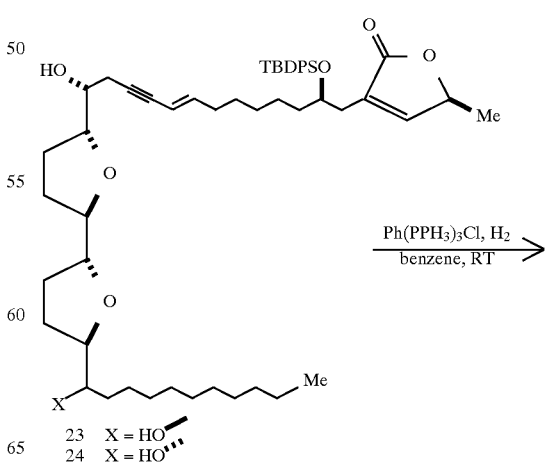

-continued

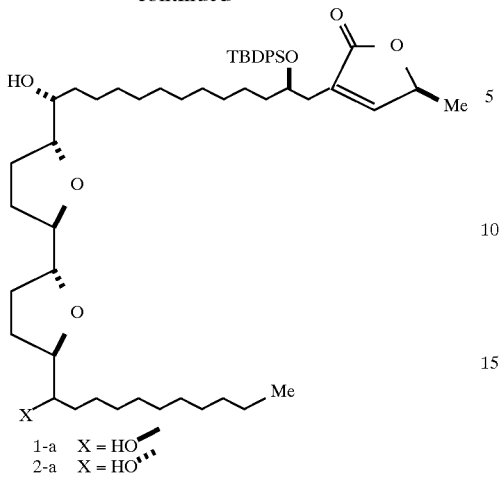

1-a  X = HO⫽
2-a  X = HO⫽

(a) To a stirred solution of 23 (60 mg, 70 mmol) in benzene (1 mL) at RT was added tris(triphenylphosphine) rhodium (I) chloride (29 mg, 32 mmol, 45 mol %). The system was flushed with Argon gas and then charged with hydrogen gas. After 24 h at RT the reaction mixture was diluted with water (10 mL) and ether (10 mL), the organic layer was separated, and the aqueous layer was extracted with ethyl acetate (3×10 mL). The organic layers were combined, washed with brine, dried ($MgSO_4$), and concentrated under reduced pressure to leave a crude yellow oil. Flash chromatography (60% ethyl acetate in hexane) gave 45 mg (75%) of the saturated 1-a as a yellow oil. $[\alpha]_D^{RT}$= −4.2° (c=0.82, $CHCl_3$); IR (neat) 3471, 3070, 3049, 1757, 1463, 1109, and 1072 $cm^{-1}$; $^1H$ NMR (300 MHz, $CDCl_3$) δ 7.65 (t, J=7 Hz, 4 H, ArH), 7.39 (m, 6 H, ArH), 6.92 (br s, 1 H, HC═CC═O), 4.88 (q, J=5.8 Hz, 1 H, $OCHH_3$), 4.02 [dddd, J=5.7, 5.7, 5.7, and 5.7 Hz, 1 H, C(4)H], 3.88–3.81 [m, 4H, C(16, 19, 20, 23)H], 3.39 [m, 2 H, C(15, 24)H], 2.57 (br s, 2 H, OH), 2.43 [br d, J=4.5 Hz, 2 H, C(3)$H_2$], 2.04–1.96 [m, 5H, from among C(17, 18, 21, 22)$H_2$], 1.71–1.60 [m, 3 H, from among C(17, 18, 21, 22)$H_2$], 1.49–1.05 [m, 38 H, C(5–14, 25–33)$H_2$], 1.04 [s, 9 H, $SiPh_2C(CH_3)_3$], and 0.88 (t, J=6.3 Hz, 3 H, $CH_2CH_3$); $^{13}C$ NMR ($CDCl_3$, 75.5 MHz) δ 173.99, 151.19, 135.87, 135.83, 134.14, 134.08, 130.66, 129.65, 127.56, 83.16, 81.78, 77.47, 74.05, 71.53, 36.38, 33.45, 31.91, 31.79, 29.73, 29.61, 29.50, 29.44, 29.33, 28.97, 28.36, 27.02, 25.66, 24.86, 22.68, 19.36, 18.91, and 14.12.

(b) Compound 2-a was prepared the same way as 1-a from the hydrogenation of 24 (35 mg, 41 mmol). Flash chromatography (60% ethyl acetate in hexane) gave 33 mg (94%) of 2-a as a yellow oil: $[\alpha]_D^{RT}$=−5.03 (c=0.46, $CHCl_3$); IR (neat) 3472, 3069, 3050, 1756,1428, 1108, and 1105 $cm^{-1}$; $^1H$ NMR (500 MHz, $CDCl_3$) δ 7.65 (t, J=7 Hz, 4 H, ArH), 7.39 (m, 6 H, ArH), 6.92 (br s, 1 H, HC═CC═O), 4.88 (q, J=5.8 Hz, 1 H, $OCHH_3$), 4.03–3.80 [m, 6 H, C(4, 16, 19, 20, 23, 24)H], 3.41 [m, 1 H, C(15), 2.85 (br s, 1 H, OH), 2.59 (br s, 1 H, OH;, 2.43 [br d, J=4.5 Hz, 2 H, C(3)$H_2$, 2.01–1.70 [m, 5 H, from among C(17, 18, 21, 22)$H_2$, 1.68–1.05 [m, 4 1H, from among C(17, 18, 21, 22)$H_2$ and C(5–14, 25–33) $H_2$], 1.04 [s, 9 H, $SiPh_2C(CH_3)_3$], and 0.88 (t, J=6.3 Hz, 3 H, $CH_2CH_3$); $^{13}C$ NMR ($CDCl_3$, 75.5 MHz) δ 174.01, 151.19, ;135.87, 135.82, 134.14, 134.09, 130.66, 129.65, 127.56, 83.31, 82.81, 82.52, 82.27, 77.04, 74.16, 71.75, 71.30, 36.38, 33.27, 32.41, 31.90, 31.78, 29.75, 29.69, 29.61, 29.50, 29.44, 29.33, 28.98, 28.40, 27.02, 26.06, 25.67, 24.86, 24.47, 22.68, 19.36, 18.90, and 14.12.

EXAMPLE 39

(+)-[2R-[2α[2'R*,5'R*(R*)],5β1(S*),2R*,13R*]]]-3-[13-[5'-[1-(Hydroxy)undecyl]octahydro[2.2'-bifuran]-5-yl]-2,13-dihydroxytridecyl]dihydro-5-methyl-2(5H)-furanone (Asimicin 1) and (+)-[2α2'R*,5'R*(S*),2R*,13R*]]]-3-[13-[5'-[1-(Hydroxy)undecyl] octahydro[2.2'-bifuran]-5-yl-2,13-dihydroxytridecyl]dihydro-5-methyl-2(5H)-furanone (Bullatacin 2)

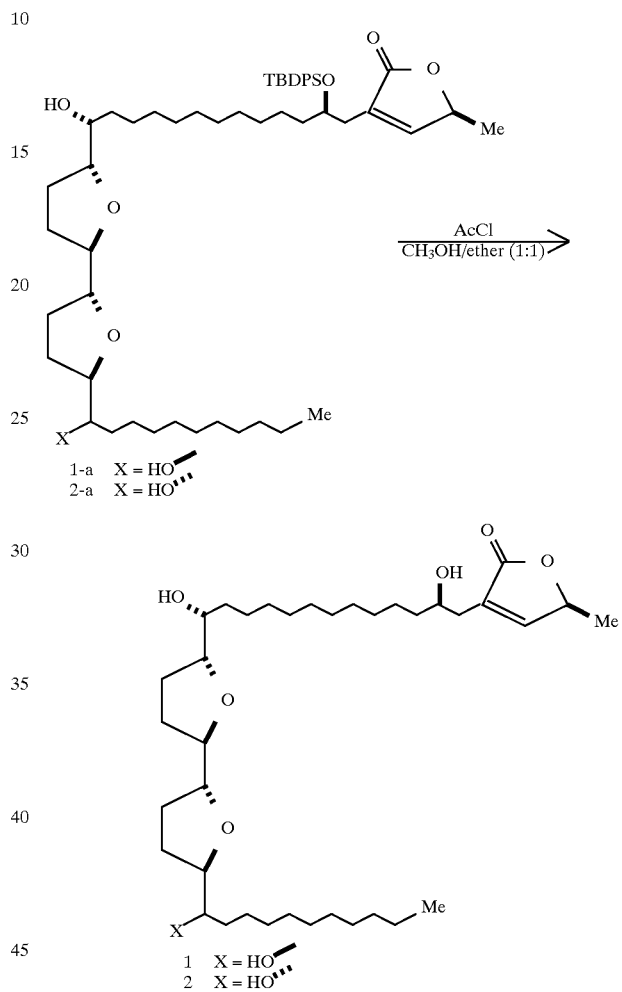

(a) To a solution of acetyl chloride (0.1 mL) in 2.1 mL of methanol, a solution of 1-a (40 mg, 46.5 nunol) in 2.1 mL of diethyl ether was added at room temperature. The solution was stirred at room temperature until TLC showed that no more starting material was left (about 24 h). Solid sodium bicarbonate was slowly added until neutral. The mixture was concentrated under reduced pressure. Diethyl ether (10 mL) was added, and the resulting solution was washed with water (2×5 mL) , dried over anhydrous magnesium sulfate, filtered, and concentrated. The residue was purified by flash chromatography (50% ethyl acetate in hexane then pure ethyl acetate) to give 25 mg (86%) of asimicin 1 as a white solid: mp 68.2°–68.4° C.; $[\alpha]_D^{RT}$=+14.7° (c=0.31, $CHCl_3$), IR (neat) 3443, 2924, 1735, and 1435 $cm^{-1}$; $^1H$ NMR ($CDCl_3$, 500 MHz) δ 7.18 (ddd, J=1.5, 1.5, and 1.5 Hz, 1 H, CH═C), 5.05 [dddq, J=1.5, 1.5, 1.5, and 7.0 Hz, 1 H, OC(36)$HCH_3$], 3.88–3.81 [m, 5 H, C(4, 16, 19, 20, 23)H], 3.38 [m, 2 H, C(15, 24)H], 2.52 [dddd, J=15.3, 4.9, 1.5, and 1.5 Hz, 1 H, C(3)$H_aH_b$], 2.40 [dddd, J=15.3, 8.3, 1.5, and 1.5

Hz, 1H,C(3)H$_b$H$_a$], 1.99–1.95 [m, 5 H, from among C(17–18, 21–22)H$_2$], 1.70–1.60 [m, 3 H, from among C(17–18, 21–22)H$_2$], 1.53–1.43 [m, 6 H, C(5, 14, 25)H$_2$], 1.42 (d, J=6.8 Hz, 3 H, OCHCH$_3$), 1.41–1.25 [m, 32 H, C(6–13, 26–33)H$_2$], 0.87 (t, J=7.0 Hz, 3H, CH$_2$CH$_3$); $^{13}$C NMR (CDCl$_3$, 75.5 MHz) δ 174.59, 151.75, 131.24, 83.17, 81.74, 77.95, 74.07, 70.00, 37.44, 33.52, 31.93, 29.64, 29.53, 29.34, 28.92, 28.50, 25.65, 22.69, 19.12, and 14.11.

(b) Bullatacin 2 was prepared the same way as 1 from 2-a (30 mg, 35 mmol). Flash chromatography (50% ethyl acetate in hexane then pure ethyl acetate) gave 17 mg (78%) of 1 as a white solid: mp 68.7°–67.0° C.; [α]$_D^{RT}$=+12.8° (c=0.26, CHCl$_3$), IR (neat) 3443, 2924, 1735, and 1435 cm$^{-1}$; $^1$H NMR (CDCl$_3$, 500 MHz) δ 7.18 (ddd, J=1.5, 1.5, and 1.5 Hz, 1 H, C=CO, 5.06 [dddq, J=1.5, 1.5, 1.5, and 6.7 Hz, 1 H, OC(36)HCH$_3$], 3.93 [m, 2H, C(19 or 20, and 23)H], 3.85 [m, 4H, C(4, 16, 19 or 20, and 24)H], 3.39 [dddd, J=7.5, 6.1, 4.3, and 1.5 Hz, 1 H, C(15)H], 2.53 [dddd, J=15.4, 3.4, 1.5, and 1.5 Hz, 1 H C(15)H$_a$H$_b$], 2.40 [dddd, J=15.2, 8.3, 1.5, and 1.5 Hz, 1 H, C(3)H$_a$H$_b$], 2.30 (br s, 2 H, OH), 2.20 (br s, 1 H, OH), 1.98 [m, 4H, from among C(17–18, 21–22)H$_2$], 1.89 [m, 1H, from among C(17–18, 21–22)H$_2$], 1.80 [m, 1H, from among C(17–18, 21–22)H$_2$], 1.60 [m, 2H, from among C(17–18, 21–22)H$_2$], 1.49 [m, 4H, from among C(5, 13, 26)$_2$], 1.45–1.28 [m, 6H, from among C(13, 14, 25), 26)H$_2$], 1.42 [d, 3H, J=6.1 Hz, CHC(37)H$_3$], 1.26 [m, 28H, C(6–12, 27–33)H$_2$], and 0.88 [t, 3H, J=7.3 Hz, C(34)H$_3$]; $^{13}$C NMR (CDCl$_3$, 75.5 MHz) δ 174.54, 151.7, 131.23, 83.20, 82.80, 82.46, 82.23, 77.91, 74.08, 71.40, 70.00, 37.42, 33.39, 32.47, 31.89, 29.67, 29.59, 29.50, 29.31, 28.87, 28.35, 26.03, 25.62, 24.54, 22.66, 19.10, and 14.07; HRMS (CI, NH$_3$ as ionizing gas) calcd for C$_{37}$H$_{70}$NO$_7$ (M+NH$_4^+$): 640.5152. Found: 640. 5161.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula:

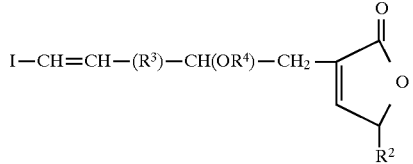

wherein R$^3$ is alkyl or aryl, R$^4$ is H or a removable hydroxyl protecting group and R$^2$ is alkyl or aryl.

2. The compound of claim 1 wherein R$^2$ is methyl.
3. The compound of claim 1 wherein (R$^3$) is (CH$_2$)$_{3-7}$.
4. The compound of claim 1 wherein R$^4$ is H.

* * * * *